(12) United States Patent
Diao et al.

(10) Patent No.: US 9,371,340 B2
(45) Date of Patent: *Jun. 21, 2016

(54) DEHYDROGENATIVE SILYLATION, HYDROSILYLATION AND CROSSLINKING USING COBALT CATALYSTS

(71) Applicants: Momentive Performance Materials Inc., Waterford, NY (US); Princeton University, Princeton, NJ (US)

(72) Inventors: Tianning Diao, New York, NY (US); Paul J. Chirik, Princeton, NJ (US); Aroop Kumar Roy, Mechanicville, NY (US); Kenrick Lewis, Flushing, NY (US); Susan Nye, Feura Bush, NY (US); Keith J. Weller, Rensselaer, NY (US); Johannes G. P. Delis, Bergen op Zoom (NL); Renyuan Yu, Beijing (CN)

(73) Assignees: Momentive Performance Materials Inc., Waterford, NY (US); Princeton University, Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/547,696

(22) Filed: Nov. 19, 2014

(65) Prior Publication Data
US 2015/0080536 A1  Mar. 19, 2015

Related U.S. Application Data

(63) Continuation-in-part of application No. 14/270,710, filed on May 6, 2014, which is a continuation-in-part of application No. 13/966,568, filed on Aug. 14, 2013, now Pat. No. 8,927,674.

(60) Provisional application No. 61/819,761, filed on May 6, 2013, provisional application No. 61/819,753, filed on May 6, 2013, provisional application No. 61/683,882, filed on Aug. 16, 2012, provisional application No. 61/906,210, filed on Nov. 19, 2014.

(51) Int. Cl.
| | |
|---|---|
| *C08G 65/22* | (2006.01) |
| *C07F 7/08* | (2006.01) |
| *C07F 7/18* | (2006.01) |
| *B01J 31/18* | (2006.01) |
| *C07F 15/06* | (2006.01) |
| *C08L 83/04* | (2006.01) |
| *C08L 83/14* | (2006.01) |
| *C08G 59/00* | (2006.01) |
| *C08G 77/38* | (2006.01) |
| *C08G 77/12* | (2006.01) |
| *C08G 77/20* | (2006.01) |

(52) U.S. Cl.
CPC ........... *C07F 7/0829* (2013.01); *B01J 31/1815* (2013.01); *C07F 7/0849* (2013.01); *C07F 7/0852* (2013.01); *C07F 7/0854* (2013.01); *C07F 7/0879* (2013.01); *C07F 7/184* (2013.01); *C07F 7/1836* (2013.01); *C07F 7/1876* (2013.01); *C07F 15/065* (2013.01); *C08L 83/04* (2013.01); *C08L 83/14* (2013.01); *B01J 2231/323* (2013.01); *B01J 2531/0241* (2013.01); *B01J 2531/0244* (2013.01); *B01J 2531/845* (2013.01); *C08G 77/12* (2013.01); *C08G 77/20* (2013.01); *C08G 77/38* (2013.01)

(58) Field of Classification Search
CPC ..................................................... C07F 7/0829
USPC .............. 502/150, 162, 167, 405; 528/31, 32, 528/402, 405, 406
See application file for complete search history.

(56) References Cited

U.S. PATENT DOCUMENTS

| | | |
|---|---|---|
| 3,159,601 A | 12/1964 | Ashby et al. |
| 3,220,972 A | 11/1965 | Lamoreaux |
| 3,296,291 A | 1/1967 | Chalk et al. |
| 3,775,452 A | 11/1973 | Karstedt |
| 3,928,629 A | 12/1975 | Chandra et al. |
| 4,550,152 A | 10/1985 | Faltynek |
| 4,572,971 A | 2/1986 | Necoechea |
| 4,578,497 A | 3/1986 | Onopchenko et al. |
| 4,729,821 A | 3/1988 | Timmons et al. |
| 4,788,312 A | 11/1988 | Paciorek et al. |
| 5,026,893 A | 6/1991 | Paciorek |
| 5,166,298 A | 11/1992 | Friedman et al. |
| 5,331,075 A | 7/1994 | Sumpter et al. |
| 5,432,140 A | 7/1995 | Sumpter et al. |
| 5,866,663 A | 2/1999 | Brookhart et al. |
| 5,955,555 A | 9/1999 | Bennett |
| 6,103,946 A | 8/2000 | Brookhart et al. |

(Continued)

FOREIGN PATENT DOCUMENTS

| | | |
|---|---|---|
| CN | 1727349 | 2/2006 |
| EP | 0786463 | 7/1997 |
| GB | 2013207 | 8/1979 |
| TW | 200902541 | 1/2009 |
| WO | 9210544 | 6/1992 |
| WO | 02088289 | 11/2002 |
| WO | 03042131 | 5/2003 |
| WO | 2008085453 | 7/2008 |
| WO | 2011006044 | 1/2011 |
| WO | 2012071359 | 5/2012 |
| WO | 2013/043783 | 3/2013 |
| WO | 2013043846 | 3/2013 |
| WO | 2015023328 | 2/2015 |

OTHER PUBLICATIONS

Abu-Surrah et al., Journal of Organometallic Chemistry 648 (2002) 55-61.

(Continued)

*Primary Examiner* — Terressa Boykin
(74) *Attorney, Agent, or Firm* — Joseph E. Waters; McDonald Hopkins LLC

(57) ABSTRACT

Disclosed herein are cobalt complexes containing terdentate pyridine di-imine ligands and their use as efficient and selective dehydrogenative silylation, hydrosilylation, and crosslinking catalysts.

30 Claims, No Drawings

(56) References Cited

U.S. PATENT DOCUMENTS

| | | | |
|---|---|---|---|
| 6,214,761 | B1 | 4/2001 | Bennett |
| 6,265,497 | B1 | 7/2001 | Herzig |
| 6,278,011 | B1 | 8/2001 | Chen et al. |
| 6,281,303 | B1 | 8/2001 | Lavoie et al. |
| 6,297,338 | B1 | 10/2001 | Cotts et al. |
| 6,417,305 | B2 | 7/2002 | Bennett |
| 6,423,848 | B2 | 7/2002 | Bennett |
| 6,432,862 | B1 | 8/2002 | Bennett |
| 6,451,939 | B1 | 9/2002 | Britovsek |
| 6,455,660 | B1 | 9/2002 | Clutton et al. |
| 6,458,739 | B1 | 10/2002 | Kimberley et al. |
| 6,458,905 | B1 | 10/2002 | Schmidt et al. |
| 6,461,994 | B1 | 10/2002 | Gibson et al. |
| 6,472,341 | B1 | 10/2002 | Kimberley et al. |
| 6,620,895 | B1 | 9/2003 | Cotts et al. |
| 6,657,026 | B1 | 12/2003 | Kimberley et al. |
| 7,053,020 | B2 | 5/2006 | DeBoer et al. |
| 7,148,304 | B2 | 12/2006 | Kimberley et al. |
| 7,161,005 | B2 | 1/2007 | Schlingloff et al. |
| 7,247,687 | B2 | 7/2007 | Cherkasov et al. |
| 7,268,096 | B2 | 9/2007 | Small et al. |
| 7,429,672 | B2 | 9/2008 | Lewis et al. |
| 7,442,819 | B2 | 10/2008 | Ionkin et al. |
| 7,456,285 | B2 | 11/2008 | Schlingloff et al. |
| 7,696,269 | B2 | 4/2010 | Cruse et al. |
| 8,236,762 | B2 | 8/2012 | Dong et al. |
| 8,236,915 | B2 | 8/2012 | Delis et al. |
| 8,415,443 | B2 | 4/2013 | Delis et al. |
| 8,895,770 | B2 | 11/2014 | Lewis et al. |
| 2002/0058584 | A1 | 5/2002 | Bennett |
| 2006/0263675 | A1 | 11/2006 | Adzic et al. |
| 2007/0264189 | A1 | 11/2007 | Adzic et al. |
| 2008/0262225 | A1 | 10/2008 | Schlingloff et al. |
| 2008/0293878 | A1 | 11/2008 | Funk et al. |
| 2009/0068282 | A1 | 3/2009 | Schlingloff et al. |
| 2009/0296195 | A1 | 12/2009 | Fontana et al. |
| 2011/0009565 | A1 | 1/2011 | Delis et al. |
| 2011/0009573 | A1 | 1/2011 | Delis et al. |
| 2012/0130021 | A1 | 5/2012 | Tondreau et al. |
| 2012/0130105 | A1 | 5/2012 | Lewis et al. |
| 2012/0130106 | A1 | 5/2012 | Chirik et al. |
| 2013/0158281 | A1 | 6/2013 | Weller et al. |
| 2014/0051822 | A1 | 2/2014 | Atienza et al. |
| 2014/0243286 | A1 | 8/2014 | Arnold et al. |
| 2014/0243486 | A1* | 8/2014 | Roy et al. ............... 525/479 |
| 2014/0330024 | A1 | 11/2014 | Atienza et al. |
| 2014/0330036 | A1 | 11/2014 | Lewis et al. |
| 2014/0343311 | A1 | 11/2014 | Boyer et al. |
| 2015/0137033 | A1 | 5/2015 | Diao et al. |

OTHER PUBLICATIONS

Albon et al., "Metal Carbonyl Complexes Involving 2,6Bix[1 - (phenylimino)ethyl]pyridine; Bidentate Corrdination of a Potentially Tridentate Ligand" Inorganica Chimica Acta, 159 (1989) 19-22.
Alyea et al., Syn. React. Inorg. Metal-Org. Chem., 4(6), 535-544 (1974).
Archer, Andrew M. et al., "Arene Coordination in Bis(imino)pyridine Iron Complexes: Identification of Catalyst Deactivation Pathways in Iron-Catalyzed Hydrogenation and Hydrosilation," Organometallics, vol. 25, pp. 4269-4278 (2006).
Atienza, C. C. H., et al. "Synthesis, Electronic Structure, and Ethylene Polymerization Activity of Bis(imino)pyridine Cobalt Alkyl Cations" J. Angew. Chem., Int. Ed. 2011, 50, 8143.
Atienza, Carmen Hojilla, "Improving the Conditions and Expanding the Scope of Bis(imino)pyridine Iron-Catalyzed Olefin Hydrosilyation." (Dissertation) Chapter 7.
Atienza, Carsten Milsmann, Emil Labkovsky, and Paul J. Chirik, "Synthesis, Electronic Structure, and Ethylene Polymerization Activity of Bis(imino)pyridine Cobalt Alkyl Cations," Agnewandte Chem. Int. Ed. 2011, 50, 8143-8147.
Bart et al., "Electronic Structure of Bis(imino)pyridine Iron Dichloride, Monochloride, and Neutral Ligand Complexes: A Combined Structural, Spectroscopic, and Computational Study," J. Am. Chem. Soc. 2006, 128, 13901-13912.
Bail, Suzanne C. et al., "Preparation and Molecular and Electronic Structures of Iron(0) Dinitrogen and Silane Complexes and Their Application to Catalytic Hydrogenation and Hydrosilation," Journal of the American Chemical Society, vol. 126, pp. 13794-13807 (2004).
Bouwkamp M W, Iron-Catalyzed [2π+2π] Cycloaddition of α,ω-Dienes the Importance of Redox-Active Supporting Ligands, Journal of the Americal Chemical Society, 2006, V128 N41, p. 13340-13341.
Bowman et al., "Reduced N-Alkyl Substituted Bis(imino)pyridine Cobalt Complexes: Molecular and Electronic Structures for Compounds Varying by Three Oxidation States," Inorg. Chem. 2010, 49, 6110-6123, Germany.
Bowman et al., "Synthesis and Molecular and Electronic Structures of Reduced Bis(imino) pyridine Cobalt Dinitrogen Complexes: Ligand versus Metal Reduction," J. Am. Chem. Soc., 2010, 132, 1676-1684, Germany.
Britovsek et al., "Novel Olefin Polymerization Catalysts Based on Iron and Cobalt," Chem. Commun., 1998, 849-850.
Buschbeck et al., Triethylene Glycol Ether End-grafted Carbosilane Dendrimers: Synthesis and Complexation Behavior, Inorganic Chemistry Communications, vol. 7, pp. 1213-1216, Oct. 13, 2004.
Cetinkaya et al., Journal of Molecular Catalysis A: Chemical 142 (1999) 101-112.
Connelly et al., "Chemical Redox Agents for Organometallic Chemistry," Chem. Rev. 1996, 96, 877-910.
Corey, Joyce Y. et al., "Reactions of Hydrosilanes with Transition-Metal Complexes: Formation of Stable Transition-Metal Silyl Compounds," Journal of Chemical Reviews, vol. 99, pp. 175-292 (1999).
Dekamin, et al. "Organocatalytic, rapid and facile cyclotrimerization of isocyanates using tetrabutylammonium phthalimide-N-oxyl and tetraethylammonium 2-(carbamoyl) benzoate under solvent-free conditions," Catalysis Communications 12 (2010) 226-230.
Fernandez et al., "Synthesis and Reactions of Dihydrido(triethylalIyl)(1,5-cycloctadiene)—Iridium(III) Complexes: Catalysts for Dehydrogneative Silylation of Alkenese," Organometallics, 1986, 5, 1519-1520.
Field et al., One-Pot Tandem Hydroamination/Hydrosilation Catalyzed by Cationic Iridium(I) Complexes, Organometallics, vol. 22, pp. 4393-4395, Sep. 25, 2003.
Gibson, et al., "The nature of the active species in bis(imino)pyridyl cobalt ethylene polymerisation catalysts," Chem. Commun., 2001, 2252-2253.
Glatz, Ines et al., "Terpyridine-Based Silica Supports Prepared by Ring-Opening Metathesis Polymerization for the Selective Extraction of Noble Metals," Journal of Chromatography A, vol. 1015, pp. 65-71 (2003).
Haarman et al., "Reactions of [RhCl(diene)]2 with Bi- and Terdentate Nitrogen Ligands. X-ray Structures of Five-Coordinate Complexes," Am. Chem. Soc., Organometallics 1997, 16, 54-67.
Nagashima et al., "Dehydrogenative Silylation of Ketones with a Bifunctional Organosilane by Rhodium-Pybox Catalysts," Chem. Soc. of Jpn., Chemistry Letters, 1993, 347-350, Toyohashi, Aichi.
Hosokawa, Satomi et al., A Chiral Iron Complex Containing a Bis(oxazolinyl)phenyl Ligand: Preparation and Asymmetric Hydrosilylation of Ketones. Organometallics, 29, 5773-5775 (2010).
Humphries et al., "Investigations into the Mechanism of Activation and Initiation of Ethylene Polymerization by Bis (imino)pyridine Cobalt Catalysts: Synthesis, Structures, and Deuterium Labeling Studies," Organometallics 2005, 24, 2039-2050, London, United Kingdom.
Jairam et al., "Ester Hydrolysis with 2,6-di(pyrazol-3-yl)pyridines and their Co 11 Complexes in Homogeneous and Micellar Media," Journal of Inorganic Biochemistry 84, 2001, 113-118, Toronto, Ontario, Canada.
Kakiuchi et al., "Completely Selective Synthesis of (E)-B-(triethylsilyl)styrenes by Fe3(CO)12-catalyzed Reaction of Styrenes With Triethylsilane," Journal of Organometallic Chemistry 1993, 456, 45-47, Osaka, Japan.
Kakiuchi et al., "Dehydrogenative Silylation of 1,5-Dienes with Hydrosilanes Catalyzed by RhCl (PPh3)3," Am. Chem. Soc., Organometallics, 1993, 12, 4748-4750, Kagawa, Japan.

(56) References Cited

OTHER PUBLICATIONS

Kaul et al., "Immobilization of Bis(imino)pyridyliron (II) complexes on Silica," Organometallics, 2002, 21(1), 74-83.
Kickelbick et al., New J. Chem., 2002, 26, 462-468.
Kim, Chungkyun et al., "2,2':6',2"-Terpyridine and Bis(2,2':6',2"-terpyridine)Ruthenium(II) Complex on the Dendritic Periphery," Journal of Organometallic Chemistry, vol. 673, pp. 77-83 (2003).
Kooistra et al., Inorganica Chimica Acta 357 (2004) 2945-2952.
Kroll, Roswitha et al., "Access to Heterogeneous Atom-Transfer Radical Polymerization (ATRP) Catalysts Based on Dipyridylamine and Terpyridine via Ring-Opening Metathesis Polymerization (ROMP)," Macromolecular Chemistry and Physics, vol. 202, pp. 645-653 (2001).
Kuo, et al., "Electrochemical studies of nickel bis(2,2':6',2"-terpyridine) with alkyl/aryl/allyl bromides and activeated olefins in nonaqueous solvents" Jiemian Kexue Huishi, vol. 15, Issue 1, pp. 23-42, Journal, 1992, Coden: CMKCEW, ISSN: 1026-325X.
Lapointe, et al., "Mechanistic Studies of Palladium(II)-Catalyzed Hydrosiliation and Dehydrogenative Silation Reactions," J. Amer. Chem. Soc. 119 (1997), pp. 906-917.
Lewis et al., "Hydrosilylation Catalized by Metal Colloids: A Relative Activity Study," Organometallics, 9 (1990), 621-625.
Lions et al., J. Chem. Soc. (A) 1957, vol. 79, 2733-2738.
Lu et al., "Iridium-Catalyzed (Z)-Trialkylsilylation of Terminal Olefins," J. Org. Chem, 2010, 75, 1701-1705, Dallas, Texas.
Lu et al., "The Molecular Structure of a Complex of a 2,6-Diimino-Pyridine as a Bidentate Lignad with Molybdenum Carbonyl" Inorganica Chimica Acta, 134 (1987) 229-232.
McAtee et al., "Preparation of Allyl and Vinyl Silanes by the Palladium-Catalyzed Silylation of Terminal Olefins: A Silyl-Heck Reaction," Angewandte Chemie, Int. Ed. 2012, 51, 3663-3667.
Naumov et al., "Selective Dehydrogentative Silylation-Hydrogenation Reaction of Divinyldisiloxane with Hydrosilane Catalyzed by an Iron Complex," Journal of the American Chemical Society, 2012, vol. 134, Issue 2, 804-807, Osaka, Japan.
Nesmeyanov. A. N. et al., "Addition, Substitution, and Telomerization Reactions of Olefins in the Presence of Metal Carbonyls or Colloidal Iron," Tetrahedron, vol. 17, pp. 1-68 (1962).
Oro, L. A., et al. "Hydrosilylation of Alkenese by Iridium Complexes," J. Mol. Catalysis, 1986, 37, 151-156.
Pal, et al., Preparation and hydrosilylation activity of a molybdenum carbonyl complex that features a pentadentate bis (amino)pyridine lignad. Inorg Chem. Sep. 2, 2014; 53(17):9357-65. doi: 10.1021/ic501465v. Epub Aug. 20, 2014.
Pangborn, et al., "Safe and Convenient Procedure for Solvent Purification," Oraganometallics, 15:1518 (1996).
Randolph, Claudia L. et al., "Photochemical Reactions of (η5-Pentamethylcyclopentadienyl)dicarbonyliron-Alkyl and Silyl Complexes: Reversible Ethylene Insertion into an Iron-Silicon Bond and Implications for the Mechanism of Transition-Metal-Catalyzed Hydrosilation of Alkenes," Journal of the American Chemical Society, vol. 108, pp. 3366-3374 (1986).
Russell et al., "Synthesis of Aryl-Substituted Bis(imino)pyridine Iron Dinitrogen Complexes," Inorg. Chem. 2010, 49, 2782-2792.
Sacconi et al., "High-spin Five-Co-Ordinate Nickel (II) and Cobald (II) Complexes with 2,6-Diacetylepyridinebis (imines)," J. Chem. Soc. (A), 1968, 1510-1515.
Seckin, Turgay; Oezdemir, Ismail; Koeytepe, Sueleyman; Guerbuez, Nevin, Preparation and Catalytic Properties of a Ru(II) Coordinated Polyimide Supported by a Ligand Containing Terpyridine Units, Journal of Inorganic and Organometallic Polymers and Materials, Apr. 9, 2009, 19(2), 143-151.
Seki et al., "Single-Operation Synthesis of Vinyl silanes from Alkenes and Hydrosilanes with the Aid of Ru (CO)12," Am. Chem. Soc., J. Org. Chem. 1986, 51, 3890-3895, Osaka, Japan.
Sieh, et al., Metal-Ligand Electron Transfer in 4d and 5d Group 9 Transition Metal Complexes with Pyridine, Diimine Ligands. Eur. J. Inorg. Chem., 2012:444-462. doi 10.1002/ejic.201101072.

Speier, John L., et al., "The Addition of Silicon Hydrides to Olefinic Double Bonds. Part II. The Use of Group VIII Metal Catalysts," Journal of the American Chemical Society, vol. 79, pp. 974-979 (1956).
Suzuki, et al., "Random and block copolymerizations of norbornene with conjugated 1,3-dienes catalyzed by novel No compounds involving N- or O-donated ligands" Reactive & Functional Polymers 59 (2004) 253-266, May 6, 2004.
Thammavongsy, et al., Ligand-Based Reduction of CO2 and Release of CO and Iron(II). Inorg. Chem., 2012, 51 (17), pp. 9168-9170. DOI: 10:1021/ic3015404. Publication Date (Web): Aug. 20, 2012.
Toma et al., J. Braz. Chem. Soc., vol. 7, No. 6, 391-394, 1996.
Tondreau et al., "Bis(imino)pyridine Iron Complexes for Aldehyde and Ketone Hydrosilylation," Am. Chem. Soc., 2008, vol. 10, No. 13, 2789-2792.
Tondreau et al: "Iron Catalysts for Selective Anti-Markovnikov Alkene Hydrosilylation Using Tertiary Silanes," Science, vol. 335, No. 6068, Feb. 2, 2012. pp. 567-570.
Tondreau, et al "Synthesis and electronic structure of cationic, neutral, and anionic bis (imino)pyridine iron alkyl complexes: evaluation of redox activity in single-component ethylene polymerization catalysts." J Am Chem Soc. Oct. 27, 2010; 132(42): 15046-59. doi: 10.1021/ja106575b.
Tondreau, et al., "Enantiopure Pyridine Bis(oxazoline) "Pybox" and Bis(oxazoline) "Box" iron Dialkyl Complexes: Comparison to Bis(imino)pyridine Compounds and Application to Catalytic Hydrosilylation of Ketones," Organometallics, Jun. 9, 2009, 28(13), 3928-3940.
Yeung, et al., "Cobalt and iron complexes of chiral C1- and C2-terpyridines: Synthesis, characterizationa dn use in catalytic asymmetric cyclopropanation of styrenes." Inorganica Chimica Acta 362 (2009) 3267-3273.
Zhu et al., "A Measure for a-Donor and -Acceptor Properties of Diiminepyridine-Type Ligands," Organometallics 2008, 27, 2699-2705.
ISA / EPO, International Search Report and Written Opinion for PCT/US2014/066338 dated May 28, 2015.
Atienza, et al., "Olefin hydrosilylation and dehydrogenative silylation with bis(imino) pyridine iron and cobalt catalysts," Abstracts of Papers, 244th ACS National Meeting & Exposition, Philadelphia, PA, Aug. 19-23, 2012.
Atienza, "Reactivity of Bis(Iminio)Pyridine Cobalt Complexes in C—H Bond Activation and Catalytic C—C and C—Si Bond Formation" PhD thesis, Jun. 2013, Princeton University.
Shaikh et al., "Iron-Catalyzed Enantioselevtive Hydrosilylation of Keytones," Angew. Chem. Int. Ed., 2008, 47, 2497-2501.
De Bo et al., "Hydrosilylation of Alkynes Mediated by N-heterocyclic Carben Platinum(0) Complexes," Organometallics, 2006, 25, 1881-1890.
Boudjouk et al., "Exclusive β-hydrosilylation of acrylates catalysed by copper-tetramethylethylenediamine," Journal of Organometallic Chemistry, Jan. 1, 1993, pp. 41-43.
Brookhart et al., "Mechanism of a cobalt(III)-catalyzed olefin hydrosilation reaction: direct evidence for a silyl migration pathway," J. Am. Chem. Soc. 1993, 115, 2151.
Castro, Pascel M. et al., "Iron-Based Catalysts Bearing Bis(imido)-Pyridine Ligands for the Polymerization of tert-Butyl Acrylate," Journal of Polymer Science: Part A: Polymer Chemistry, vol. 41, pp. 1380-1389 (2003).
Cornish, et al., "Homogeneous catalysis: VI. Hydrosilylation using tri(pentanedionato)rhodium(III) or tetrakis(µ-acetato) Dirhodium(II) as Catalysts," Journal of Organometallic Chemistry, Elsevier-Sequoia S.A. Lausanne, CH, vol. 172, No. 2, Jun. 12, 1979, pp. 153-163.
Chuit et al. "Reactivity of penta- and hexacoordinate silicon compounds and their role as reaction intermediates," Chem. Rev. 1993, 93, 1371-1448.
De Rycke et al., "Toward reactant encapsulation for substrate-selectivity," Tetrahedron Lett. 2012, 53, 462.
Doucette, "Homogeneous Iron Catalysts With Redox-Active Ligands: Synthesis and Electronic Structure," Dissertation Cornell University, Aug. 2006.

(56) References Cited

OTHER PUBLICATIONS

Doyle et al, "Addition/Elimination in the Rhodium(II) Perfluorobutyrate Catalyzed Hydrosilylationo of 1-Alkenes. Rhodium Hydride Promoted Isomerization and Hydrogenation," Organometallics, 1992, 11, 549-555, San Antonio, Texas.

Falck, J. R. et al. "Iridium-Catalyzed (Z)-Trialkylsilylation of Terminal Olefins," J. Org. Chem. 2010, 75, 1701.

Figgins et al., "Complexes of Iron(II), Cobalt(II) and Nickel(II) with Biacetyl-bis-methlylimine, 20Pyridinal-methylimine and 2,6-Pyridindial-bis-methylimine" J. Am. Chem. Soc. 1960, vol. 82, 820-824.

Gandon, et al., "Silicon-Hydrogen Bond Activation and Hydrosilylation of Alkenes Mediated by CpCo Complexes: A Theoretical Study," J. Am. Chem. Soc. 2009, 131, 3007.

Hori et al, "Ruthenium Complex-Catalyzed Silylation of Olefins. Selective Sysnthesis of Allysilanes," Bull. Chem. Soc. Jpn., 1988, 61, 3011-3013, Kyoto, Japan.

Itoh et al, "Disproportionation reactions of organohydrosilanes in the presence of base catalysts" J. Organomet. Chem., 2001, 629, 1-6.

Ivchenko et al., "A convenient approach for the synthesis of 2,6-diformyl- and 2,6-diacetylpyridines," Tetrahedron Lett. 2013, 54, 217.

Fruchtel et al; "Organic Chemistry on Solid Supports," Angewandte Chemie International Edition in English, 1996, vol. 35, Issue 1, pates 17-42.

Junge et al., "Iron-Catalyzed Reduction of Carboxylic Esters to Alcohols," European Journal of Organic Chemistry, vol. 2013, No. 11, Mar. 1, 2013, pp. 2016-2065.

Knijnenburg et al., "Olefin hydrogenation using diimine pyridine complexes of Co and Rh," Journal of Molecular Catalysis, 232 (2005), No. 1-2, pp. 151-159.

Marciniec, Bogdan, "Catalysis by Transition Metal Complexes of Alkene Silylation—Recent Progress and Mechanistic Implications," Coordination Chemistry Reviews, 249 (2009) 2374-2390.

Martinez, Remi et al., "C—C Bond Formation via C—H Bond Activation Using an in Situ-Generated Ruthenium Catalyst," Journal of the American Chemical Society, vol. 131, pp. 7887-7895 (2009).

McAtee et al., "Rational Design of a Second Generation Catalyst for Preparation of Allylsilanes Using the Silyl-Heck Reaction," J. Am. Chem. Soc. 2014, 136 (28), 10166-10172.

Bareille et al., "First Titanium-Catalyzed anti-1,4-Hydrosilylation of Dienes," Organometallics, 2005, 24(24), 5802-5806.

Nishiyama et al., "An Iron-Catalysed Hydrosilylation of Ketones," Chem. Commun., Royal Society of Chemistry, 2007, 760-762.

Furuta et al., "Highly efficient catalytic system for hydrosilylation of ketones with iron(II) acetate—thiophenecarboxylate," Tetrahedron Letters, 2008, vol. 49, Issue 1, pp. 110-113.

Ojima et al., "Regioselective hydrosilylation of 1,3-dienes catalyzed by phosphine complexes of palladium and rhodium," J. Organomet. Chem. 1978, 157, 359-372.

Pettigrew, "Synthetic Lubricants and High Performance Fluids, Ch. 12 Silahydrcarbons" (second edition), L. R. Rudnick and L. R. Shubkin (Editors), Marcel Dekker, NY 1999, pp. 287-296.

Poyatos, Macarena et al., "Coordination Chemistry of a Modular N,C-Chelating Oxazole-Carbene Ligand and Its Applications in Hydrosilylation Catalysis," Organometallics, vol. 25, pp. 2634-2641 (2006).

Reiff, W. M. et al., "Mono(2,2',2"-terpyridine) Complexes of Iron(II)," Journal of Inorganic Chemistry, vol. 8, No. 9, pp. 2019-2021 (1969).

Parker et al. "1,2-Selective Hydrosilylation of Conjugated Dienes," J. Am. Chem. Soc., 2014, 136 (13), pp. 4857-4860.

Benkeser et al., "Chloroplatinic acid catalyzed additions of silanes to isoprene," J. Organomet. Chem. 1978, 156, 235-244.

Schmidt, Roland et al., "Heterogenized Iron(II) Complexes as Highly Active Ethene Polymerization Catalysts," Journal of Molecular Catalysis A: Chemical, vol. 179, pp. 155-173 (2002).

Shaikh et al., "A Convenient and General Iron-Catalyzed Hydrosilylation of Aldehydes," Organic Letters, vol. 9, No. 26, Dec. 1, 2007, pp. 5429-5432.

Small, B. L., et al. "Highly Active Iron and Cobalt Catalysts for the Polymerization of Ethylene," J. Am. Chem. Soc. 1998, 120(16), 4049-4050.

Greenhalgh et al.,"Iron-Catalysed Chemo-, Regio-, and Stereoselective Hydrosilylation of Alkenes and Alkynes using a Bench-Stable Iron(II) Pre-Catalyst," Adv. Synth. Cata. 2014, 356(2-3), 584-590.

Woo et al., "Redistribution of Bos- and Tris(silyl)methanes Catalyzed by Red-Al," Bull. Korean. Chem. Soc. 1996, 17, 123-125.

Wu et al., "A Strategy for the Synthesis of Well-Defined Iron Catalysts and Application to Regioselective Diene Hydrosilylation," Journal of the American Chemical Society, vol . 132, No. 38. Sep. 29, 2010, pp. 13214-13216.

Yi, Chae S. et al., "Regioselective Intermolecular Coupling Reaction of Arylketones and Alkenes Involving C—H Bond Activation Catalyzed by an in Situ Formed Cationic Ruthenium Hydride Complex," Organometallics, vol. 28, pp. 4266-4268 (2009).

Zhang et al., "Ferrous and Cobaltous Chlorides Bearing 2,8-Bis(imino)quinolines: Highly Active Catalysts for Ethylene Polymerization at High Temperature," Organometallics, vol. 29, pp. 1168-1173 (2010).

Zhu et al., "(Py)2Co(CH2SiMe3)2 As an Easily Accessible Source of "CoR2"," Organometallics, 2010, 29 (8), 1897-1908.

Marciniec et al. "Encyclopedia of Catalysis" pp. 6,7, and 20, Mar. 5, 2010.

* cited by examiner

US 9,371,340 B2

DEHYDROGENATIVE SILYLATION, HYDROSILYLATION AND CROSSLINKING USING COBALT CATALYSTS

CROSS REFERENCE TO RELATED APPLICATIONS

This application is a continuation-in-part of U.S. application Ser. No. 14/270,710 filed May 6, 2014, which is a continuation-in-part of U.S. application Ser. No. 13/966,568 filed on Aug. 14, 2013, which claims the benefit of Provisional Application No. 61/819,761 filed on May 6, 2013, Provisional Application No. 61/819,753 filed on May 6, 2013, and Provisional Application No. 61/683,882 filed on Aug. 16, 2012. This application also claims the benefit of Provisional Application 61/906,210 filed on Nov. 19, 2013.

FIELD OF THE INVENTION

This invention relates generally to transition metal-containing compounds, more specifically to cobalt complexes containing pyridine di-imine ligands and their use as efficient dehydrogenative silylation, hydrosilylation and crosslinking catalysts.

BACKGROUND OF THE INVENTION

Hydrosilylation chemistry, typically involving a reaction between a silyl hydride and an unsaturated organic group, is the basis for synthetic routes to produce commercial silicone-based products like silicone surfactants, silicone fluids and silanes as well as many addition cured products like sealants, adhesives, and silicone-based coating products. See, for example, US Patent Application Publication 2011/0009573A1 to Delis et al. Typical hydrosilylation reactions use precious metal catalysts to catalyze the addition of a silyl-hydride (Si—H) to an unsaturated group, such as an olefin. In these reactions, the resulting product is a silyl-substituted, saturated compound. In most of these cases, the addition of the silyl group proceeds in an anti-Markovnikov manner, i.e., to the less substituted carbon atom of the unsaturated group. Most precious metal catalyzed hydrosilylations only work well with terminally unsaturated olefins, as internal unsaturations are generally non-reactive or only poorly reactive. There are currently only limited methods for the general hydrosilylation of olefins where after the addition of the Si—H group there still remains an unsaturation in the original substrate. This reaction, termed a dehydrogenative silylation, has potential uses in the synthesis of new silicone materials, such as silanes, silicone fluids, crosslinked silicone elastomers, and silylated or silicone-crosslinked organic polymers such as polyolefins, unsaturated polyesters, and the like.

Various precious metal catalysts are known in the art. For example, U.S. Pat. No. 3,775,452 discloses a platinum complex containing unsaturated siloxanes as ligands. This type of catalyst is known as Karstedt's catalyst. Other exemplary platinum-based hydrosilylation catalysts that have been described in the literature include Ashby's catalyst as disclosed in U.S. Pat. No. 3,159,601, Lamoreaux's catalyst as disclosed in U.S. Pat. No. 3,220,972, and Speier's catalyst as disclosed in Speier, J. L, Webster J. A. and Barnes G. H., J. Am. Chem. Soc. 79, 974 (1957).

There are examples of the use of $Fe(CO)_5$ to promote limited hydrosilylations and dehydrogenative silylations. (See Nesmeyanov, A. N.; Freidlina, R. Kh.; Chukovskaya, E. C.; Petrova, R. G.; Belyaysky, A. B. *Tetrahedron* 1962, 17, 61 and Marciniec, B.; Majchrzak, M. *Inorg. Chem. Commun.* 2000, 3, 371). The use of $Fe_3(CO)_{12}$ was also found to exhibit dehydrogenative silylation in the reaction of $Et_3SiH$ and styrene. (Kakiuchi, F.; Tanaka, Y.; Chatani, N.; Murai, S. *J. Organomet. Chem.* 1993, 456, 45). Also, several cyclopentadiene iron complexes have been used to varying degrees of success, with the work of Nakazawa, et al showing interesting intramolecular dehydrogenative silylation/hydrogenation when used with 1,3-di-vinyldisiloxanes. (Roman N Naumov, Masumi Itazaki, Masahiro Kamitani, and Hiroshi Nakazawa, *Journal of the American Chemical Society,* 2012, Volume 134, issue 2; Pages 804-807).

A rhodium complex was found to give low to moderate yields of allyl-silanes and vinyl silanes. (Doyle, M. P.; Devora G. A.; Nevadov, A. O.; High, K. G. *Organometallics,* 1992, 11, 540-555). An iridium complex was also found to give vinyl silanes in good yields. (Falck, J. R.; Lu, B, *J. Org Chem,* 2010, 75, 1701-1705.) Allyl silanes could be prepared in high yields using a rhodium complex (Mitsudo, T.; Watanabe, Y.; Hori, Y. *Bull. Chem. Soc. Jpn.* 1988, 61, 3011-3013). Vinyl silanes could be prepared through the use of a rhodium catalyst (Murai, S.; Kakiuchi, F.; Nogami, K.; Chatani, N.; Seki, Y. *Organometallics,* 1993, 12, 4748-4750). Dehydrogenative silylation was found to occur when iridium complexes were used (Oro, L. A.; Fernandez, M. J.; Esteruelas, M. A.; Jiminez, M. S. *J. Mol. Catalysis,* 1986, 37, 151-156 and Oro, L. A.; Fernandez, M. J.; Esteruelas, M. A.; Jiminez, M. S. *Organometallics,* 1986, 5, 1519-1520). Vinyl silanes could also be produced using ruthenium complexes (Murai, S.; Seki, Y.; Takeshita, K.; Kawamoto, K.; Sonoda, N. *J. Org. Chem.* 1986, 51, 3890-3895.).

A palladium-catalyzed silyl-Heck reaction was recently reported to result in the formation of allyl-silanes and vinyl silanes (McAtee J R, et al., *Angewandte Chemie, International Edition in English* (Mar. 1, 2012); McAtee, J R et al., *J. Am. Chem. Soc.* 2014, 136, 10166).

U.S. Pat. No. 5,955,555 discloses the synthesis of certain iron or cobalt pyridine di-imine (PDI) complexes bearing two ionic ligands. The preferred anions are chloride, bromide and tetrafluoroborate. U.S. Pat. No. 7,442,819 discloses iron and cobalt complexes of certain tricyclic ligands containing a "pyridine" ring substituted with two imino groups. U.S. Pat. Nos. 6,461,994, 6,657,026 and 7,148,304 disclose several catalyst systems containing certain transitional metal-PDI complexes. U.S. Pat. No. 7,053,020 discloses a catalyst system containing, inter alia, one or more bisarylimino pyridine iron or cobalt catalyst. Chirik et al describe bisarylimino pyridine cobalt complexes with anionic ligands (Inorg. Chem. 2010, 49, 6110 and JACS. 2010, 132, 1676.) However, the catalysts and catalyst systems disclosed in these references are described for use in the context of olefin hydrogenation, polymerizations and/or oligomerisations, not in the context of dehydrogenative silylation reactions. Pyridine(di)imine cobalt methyl complexes with N-alkyl substituents have been reported to give mixtures of hydrosilylation and dehydrogenative silylation products when reacted with silyl-hydrides and excess olefin (Atienza, C. C. H. A, PhD thesis (2013), Princeton University). Certain derivatives of pyridine (di)imine cobalt methyl complexes with N-alkyl substituents have proven challenging to synthesize thus necessitating the production of pre-catalysts such as pyridine(di)imine cobalt neosilyl complexes.

There is a continuing need in the silylation industry for non-precious metal-based catalysts that are effective for efficiently catalyzing dehydrogenative silylations and/or hydrosilylation. The present invention provides one answer to that need.

Further, many industrially important homogeneous metal catalysts suffer from the drawback that following consumption of the first charge of substrates, the catalytically active metal is lost to aggregation and agglomeration whereby its catalytic properties are substantially diminished via colloid formation or precipitation. This is a costly loss, especially for noble metals such as Pt. Heterogeneous catalysts are used to alleviate this problem but have limited use for polymers and also have lower activity than homogeneous counterparts. For example, it is well-known in the art and in the hydrosilylation industry that the two primary homogeneous catalysts, Speier's and Karstedt's, often lose activity after catalyzing a charge of olefin and silyl- or siloxyhydride reaction. If one charge of the homogeneous catalyst could be re-used for multiple charges of substrates, then catalyst and process cost advantages would be significant.

SUMMARY OF THE INVENTION

In one aspect, the present invention is directed to a process for producing a silylated product comprising reacting a mixture comprising (a) an unsaturated compound containing at least one unsaturated functional group, (b) a silyl hydride containing at least one silylhydride functional group, and (c) a catalyst, optionally in the presence of a solvent, to produce a dehydrogenative silylated product, a hydrosilylated product, or a combination of a dehydrogenative silylated product and a hydrosilylated product, wherein the catalyst is a complex of the Formula (I) or an adduct thereof;

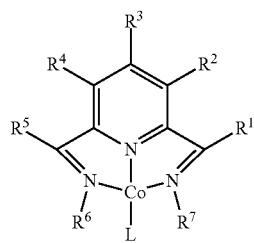

(I)

wherein each occurrence of $R^1$, $R^2$, $R^3$, $R^4$, and $R^5$) is independently hydrogen, a C1-C18 alkyl, a C1-C18 substituted alkyl, an aryl, a substituted aryl, or an inert substituent, $R^1$-$R^5$, other than hydrogen, optionally contain at least one heteroatom;

each occurrence of $R^6$ and $R^7$ is independently a C1-C18 alkyl, a C1-C18 substituted alkyl, an aryl, or a substituted aryl, wherein $R^6$ and $R^7$ optionally contain at least one heteroatom;

optionally any two of $R^1$, $R^2$, $R^3$, $R^4$, $R^5$, $R^6$, and $R^7$ vicinal to one another taken together may form a ring being a substituted or unsubstituted, saturated, or unsaturated cyclic structure; and L is $CH_2SiR^8_3$ where each occurrence of $R^8$ is independently a C1-10 alkyl or an aryl group, where $R^8$ optionally contains at least one heteroatom.

In one embodiment, $R^8$ is $CH_3$.

In one embodiment, $R^6$ and $R^7$ are independently chosen from a C1-C10 alkyl. In one embodiment, $R^6$ and $R^7$ are each methyl. In one embodiment, $R^6$ and $R^7$ are each ethyl. In one embodiment, $R^6$ and $R^7$ are each cyclohexyl.

In one embodiment, $R^8$ is methyl; $R^6$ and $R^7$ are independently chosen from a C1-C10 alkyl, and $R^2$, $R^3$, and $R^4$ are each hydrogen.

In one embodiment, the catalyst is chosen from:

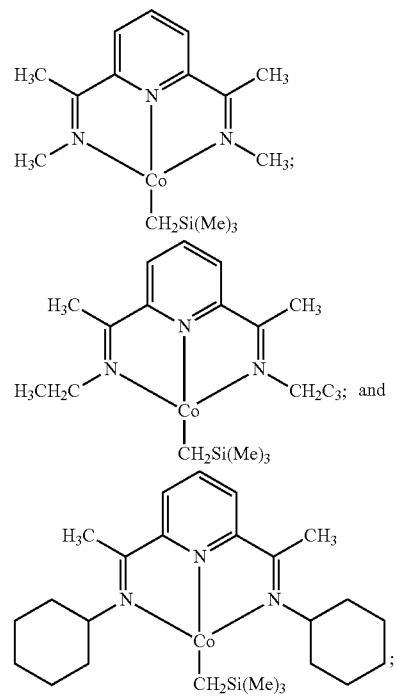

or a combination of two or more thereof.

In one embodiment, component (a) is chosen from an olefin, a cycloalkene, an unsaturated polyether, a vinyl-functional alkyl-capped allyl or methallyl polyether, an alkyl-capped terminally unsaturated amine, an alkyne, a terminally unsaturated acrylate or methacrylate, an unsaturated aryl ether, a vinyl-functionalized polymer or oligomer, a vinyl-functionalized silane, a vinyl-functionalized silicone, an unsaturated fatty acid, an unsaturated ester, or a combination of two or more thereof.

In one embodiment, component (a) is chosen from a compound of the formula:

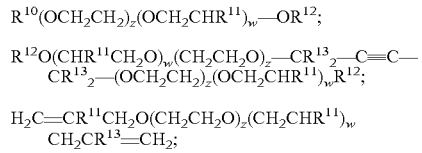

or a combination of two or more thereof, wherein $R^{10}$ is chosen from an unsaturated organic group containing from 2 to 10 carbon atoms; $R^{12}$ is chosen from hydrogen, a vinyl group, or a polyether capping group of from 1 to 8 carbon atoms; each occurrence of $R^{11}$ is independently chosen from a monovalent hydrocarbon group having 1-20 carbon atoms, an aryl group, an alkaryl, an aralkyl, a cycloalkyl group; each occurrence of $R^{13}$ is independently chosen from hydrogen, a monovalent hydrocarbon group having 1-20 carbon atoms, an aryl group, an alkaryl group, an aralkyl group, or a cycloalkyl group; each occurrence of z is 0 to 100 inclusive; and, each occurrence of w is 0 to 100 inclusive.

In one embodiment, component (a) is chosen from N,N-dimethylallyl amine, allyloxy-substituted polyethers, propylene, 1-butene, 1-hexene, styrene, vinylnorbornane, 5-vinyl-norbornene, 1-octadecene, cyclopentene, cyclohexene, norbornene, 3-hexene, isobutylene, 3-methyl-1-octene, polybutadiene, polyisoprene, EPDM, oleic acid, linoleic acid, methyl oleate, a vinyl siloxane of the Formula VI,

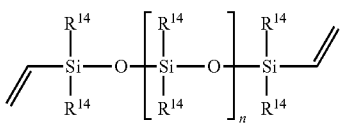

(VI)

or a combination of two or more thereof, wherein each occurrence of $R^{14}$ is independently a C1-C18 alkyl, C1-C18 substituted alkyl, vinyl, aryl, or a substituted aryl, and n is greater than or equal to zero.

In one embodiment, component (b) is chosen from a compound of the formula $R_aSiH_{4-a}$, $(RO)_aSiH_{4-a}$, $HSiR_a(OR)_{3-a}$, $R_3Si(CH_2)_f(SiR_2O)_kSiR_2H$, $(RO)_3Si(CH_2)_f(SiR_2O)_kSiR_2H$, $Q_uT_vT_p^HD_wD^H_xM^H_yM_z$, $R_3Si(CH_2R)_xSiOSiR_2(OSiR_2)_y$ $OSiR_2H$, or combinations of two or more thereof where each occurrence of R is independently a C1-C18 alkyl, a C1-C18 substituted alkyl, wherein R optionally contains at least one heteroatom, each occurrence of a independently has a value from 0 to 3, f has a value of 1 to 8, k has a value of 1 to 11, each of p, u, v, y and z independently has a value from 0 to 20, w and x are from 0 to 3000, provided that p+x+y equals 1 to 1000 and the valences of the all the elements in the silyl hydride are satisfied, M represents a monofunctional group of formula $R'_3SiO_{1/2}$, D represents a difunctional group of formula $R'_2SiO_{2/2}$; represents a trifunctional group of formula $R'SiO_{3/2}$, Q represents a tetrafunctional group of formula $SiO_{4/2}$, an $M^H$ represents $HR'_2SiO_{1/2}$, $T^H$ represents $HSiO_{3/2}$, and $D^H$ represents $R'HSiO_{2/2}$; each occurrence of R' is independently C1-C18 alkyl, C1-C18 substituted alkyl, wherein R' optionally contains at least one heteroatom; x is 1-8, and y is 0-10.

In one embodiment, the catalyst is present in an amount of from 0.01 mole percent to 10 mole percent based on the molar quantity of the unsaturated compound to be reacted.

In one embodiment, the process is conducted at a temperature of between about 0° C. and about 300° C.

In one embodiment, the complex is immobilized on a support. In one embodiment, the support is chosen from carbon, silica, alumina, $MgCl_2$, zirconia, polyethylene, polypropylene, polystyrene, poly(aminostyrene), sulfonated polystyrene, or a combination of two or more thereof.

In one aspect, the present invention provides a process for producing a hydrosilylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the dehydrogenative silylated product, and/or hydrosilylated product wherein the catalyst is a complex of the Formula (I) or an adduct thereof;

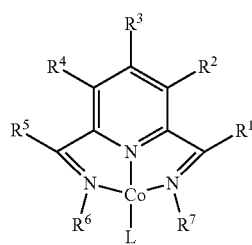

(I)

wherein each occurrence of $R^1$, $R^2$, $R^3$, $R^4$, and $R^5$ is independently hydrogen, a C1-C18 alkyl, a C1-C18 substituted alkyl, an aryl, a substituted aryl, or an inert substituent, wherein $R^1$-$R^5$, other than hydrogen, optionally contain at least one heteroatom;

each occurrence of $R^6$ and $R^7$ is independently a C1-C18 alkyl, a C1-C18 substituted alkyl, an aryl, a substituted aryl, wherein $R^6$ and $R^7$ optionally contain at least one heteroatom;

optionally any two of $R^1$, $R^2$, $R^3$, $R^4$, $R^5$, $R^6$, and $R^7$ vicinal to one another taken together may form a ring being a substituted or unsubstituted, saturated, or unsaturated cyclic structure; and L is $CH_2SiR^8_3$ where each $R^8$ is independently a C1-10 alkyl or aryl group optionally containing at least one heteroatom.

In one embodiment, component (a) is chosen from an olefin, a cycloalkene, an alkyl-capped allyl polyether, a vinyl-functional alkyl-capped allyl or methallyl polyether, an alkyl-capped terminally unsaturated amine, an alkyne, a terminally unsaturated acrylate or methacrylate, an unsaturated aryl ether, a vinyl-functionalized polymer or oligomer, a vinyl-functionalized silane, a vinyl-functionalized silicone, an unsaturated fatty acid, an unsaturated ester, or a combination of two or more thereof; and component (b) is chosen from a compound of the formula $R_aSiH_{4-a}$, $(RO)_aSiH_{4-a}$, $HSiR_a(OR)_{3-a}$, $R_3Si(CH_2)_f(SiR_2O)_kSiR_2H$, $(RO)_3Si(CH_2)_f(SiR_2O)_kSiR_2H$, $Q_uT_vT_p^HD_wD^H_xM^H_yM_z$, $R_3Si(CH_2R)_xSiO$-$SiR_2(OSiR_2)_yOSiR_2H$ and combinations of two or more thereof where each occurrence of R is independently a C1-C18 alkyl, a C1-C18 substituted alkyl, wherein R optionally contains at least one heteroatom, each occurrence of a independently has a value from 1 to 3, f has a value of 1 to 8, k has a value of 1 to 11, each of p, u, v, y and z independently has a value from 0 to 20, w and x are from 0 to 500, provided that p+x+y equals 1 to 500 and the valences of the all the elements in the silyl hydride are satisfied, M represents a monofunctional group of formula $R'_3SiO_{1/2}$, a D represents a difunctional group of formula $R'_2SiO_{2/2}$, T represents a trifunctional group of formula $R'SiO_{3/2}$, Q represents a tetrafunctional group of formula $SiO_{4/2}$, an $M^H$ represents $HR'_2SiO_{1/2}$, $T^H$ represents $HSiO_{3/2}$, and $D^H$ represents $R'HSiO_{2/2}$; each occurrence of R' is independently a C1-C18 alkyl, a C1-C18 substituted alkyl, wherein R' optionally contains at least one heteroatom In one embodiment, component (a) is chosen from a vinyl-functionalized silane, a vinyl-functionalized silicone, or a combination thereof.

In one embodiment, component (a) is chosen from a vinyl siloxane of the formula

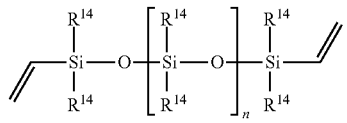

wherein each occurrence of $R^{14}$ is independently a C1-C18 alkyl, a C1-C18 substituted alkyl, a vinyl, an aryl, a substituted aryl, and n is greater than or equal to zero.

In one embodiment, $R^6$ and $R^7$ are each methyl.

In one embodiment, component (b) comprises a trialkoxy silyl hydride.

In one embodiment, component (a) is chosen from an olefin, a cycloalkene, an alkyl-capped allyl polyether, a vinyl-functional alkyl-capped allyl or methallyl polyether, an alkyl-capped terminally unsaturated amine, an alkyne, a terminally unsaturated acrylate or methacrylate, an unsaturated aryl ether, a vinyl-functionalized polymer or oligomer, a vinyl-functionalized silane, a vinyl-functionalized silicone, an unsaturated fatty acid, an unsaturated ester, or a combination of two or more thereof.

In one embodiment, the catalyst is present in an amount of from 0.01 mole percent to 10 mole percent based on the molar quantity of the unsaturated compound to be reacted.

In one embodiment, the process is conducted at a temperature of between about 0° C. and about 300° C.

In one aspect, the present invention provides a process for producing a crosslinked material, comprising reacting a mixture comprising (a) a silyl-hydride containing polymer, (b) a mono-unsaturated olefin or an unsaturated polyolefin, or combinations thereof and (c) a catalyst, optionally in the presence of a solvent, in order to produce the crosslinked material, wherein the catalyst is a complex of the Formula (I) or an adduct thereof:

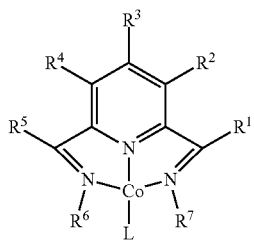

wherein each occurrence of $R^1$, $R^2$, $R^3$, $R^4$, and $R^5$ is independently hydrogen, a C1-C18 alkyl, a C1-C18 substituted alkyl, an aryl, a substituted aryl, or an inert substituent, wherein $R^1$-$R^5$, other than hydrogen, optionally contain at least one heteroatom;

each occurrence of $R^6$ and $R^7$ is independently a C1-C18 alkyl, a C1-C18 substituted alkyl, aryl or substituted aryl, wherein $R^6$ and $R^7$ optionally contain at least one heteroatom;

optionally any two of $R^1$, $R^2$, $R^3$, $R^4$, $R^5$, $R^6$, and $R^7$ vicinal to one another taken together may form a ring being a substituted or unsubstituted, saturated, or unsaturated cyclic structure; and L is $CH_2SiR^8{}_3$ where each $R^8$ is independently a C1-10 alkyl or aryl group optionally containing at least one heteroatom.

In one embodiment, the reaction is conducted under an inert atmosphere.

In one embodiment, the reaction is conducted in the presence of a solvent selected from the group consisting of hydrocarbons, halogenated hydrocarbons, ethers, and combinations thereof.

In one embodiment, the reaction is carried out at a temperature of 0° C. to 300° C.

In one embodiment, the catalyst is present in an amount of from about 0.1 mol % to about 5 mol %.

DETAILED DESCRIPTION OF THE INVENTION

The invention relates to cobalt complexes containing pyridine di-imine ligands and their use as efficient dehydrogenative silylation, hydrosilylation, and crosslinking catalysts. In one embodiment of the invention, there is provided a complex of the Formulae (I) or (II), wherein Co may be in any valence or oxidation state (e.g., +1, +2, or +3) for use in said dehydrogenative silylation, hydrosilylation, and crosslinking reactions. In particular, according to one embodiment of the invention, a class of cobalt pyridine di-imine complexes has been found that are capable of dehydrogenative silylation and/or hydrosilylation reactions.

By "alkyl" herein is meant to include straight, branched and cyclic alkyl groups. Specific and non-limiting examples of alkyls include, but are not limited to, methyl, ethyl, propyl, isobutyl and cyclohexyl.

By "substituted alkyl" herein is meant an alkyl group that contains one or more substituent groups that are inert under the process conditions to which the compound containing these groups is subjected. The substituent groups also do not substantially or deleteriously interfere with the process.

By "aryl" herein is meant a non-limiting group of any aromatic hydrocarbon from which one hydrogen atom has been removed. An aryl may have one or more aromatic rings, which may be fused, connected by single bonds or other groups. Specific and non-limiting examples of aryls include, but are not limited to, tolyl, xylyl, phenyl and naphthalenyl.

By "substituted aryl" herein is meant an aromatic group substituted as set forth in the above definition of "substituted alkyl." Similar to an aryl, a substituted aryl may have one or more aromatic rings, which may be fused, connected by single bonds or other groups; however, when the substituted aryl has a heteroaromatic ring, the free valence in the substituted aryl group can be to a heteroatom (such as nitrogen) of the heteroaromatic ring instead of a carbon. If not otherwise stated, it is preferred that substituted aryl groups herein contain 1 to about 30 carbon atoms.

By "alkenyl" herein is meant any straight, branched, or cyclic alkenyl group containing one or more carbon-carbon double bonds, where the point of substitution can be either a carbon-carbon double bond or elsewhere in the group. Specific and non-limiting examples of alkenyls include, but are not limited to, vinyl, propenyl, allyl, methallyl, ethylidenyl norbornane.

By "alkynyl" is meant any straight, branched, or cyclic alkynyl group containing one or more carbon-carbon triple bonds, where the point of substitution can be either at a carbon-carbon triple bond or elsewhere in the group.

By "unsaturated" is meant one or more double or triple bonds. In one embodiment, it refers to carbon-carbon double or triple bonds.

By "inert substituent" herein is meant a group other than hydrocarbyl or substituted hydrocarbyl, which is inert under the process conditions to which the compound containing the group is subjected. The inert substituents also do not substantially or deleteriously interfere with any process described herein that the compound in which they are present may take part in. Examples of inert substituents include halo (fluoro, chloro, bromo, and iodo), ether such as —$OR^9$ wherein $R^9$ is hydrocarbyl or substituted hydrocarbyl.

By "hetero atoms" herein is meant any of the Group 13-17 elements except carbon, and can include for example oxygen, nitrogen, silicon, sulfur, phosphorus, fluorine, chlorine, bromine, and iodine.

By "olefin" herein is meant any aliphatic or aromatic hydrocarbon also containing one or more aliphatic carbon-carbon unsaturations. Such olefins may be linear, branched or cyclic and may be substituted with heteroatoms as described above, with the proviso that the substituents do not interfere substantially or deleteriously with the course of the desired reaction to produce the dehydrogenatively silylated and/or hydrosilylated product. In one embodiment, the unsaturated compound useful as a reactant in the dehydrogenative silylation/hydrosilylation is an organic compound having the structural group, $R_2C\!=\!C\!-\!CHR$, where R is an organic fragment or hydrogen.

As indicated above, the present invention is directed to a process for producing a dehydrogenatively silylated and/or hydrosilylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the dehydrogenative silylated product, and/or hydrosilylated product wherein the catalyst is a complex of the Formula (I) or an adduct thereof;

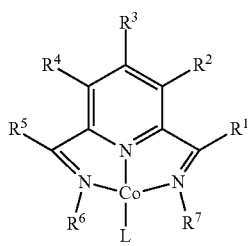

(I)

wherein each occurrence of $R^1$, $R^2$, $R^3$, $R^4$, and $R^5$ is independently hydrogen, C1-C18 alkyl, C1-C18 substituted alkyl, aryl, substituted aryl, or an inert substituent, wherein $R^1$-$R^5$, other than hydrogen, optionally contain at least one heteroatom;

each occurrence of $R^6$ and $R^7$ is independently C1-C18 alkyl, C1-C18 substituted alkyl, aryl or substituted aryl, wherein $R^6$ and $R^7$ optionally contain at least one heteroatom;

optionally any two of $R^1$, $R^2$, $R^3$, $R_4$, $R_5$, $R^6$ and $R^7$ vicinal to one another taken together may form a ring being a substituted or unsubstituted, saturated, or unsaturated cyclic structure; and L hydroxyl, chloride, bromide, or a C1-C18 alkyl, C1-C18 substituted alkyl, aryl, or substituted aryl group, or component (a) wherein L optionally contains at least one heteroatom.

In one embodiment, L is $CH_2SiR^8_3$ where each $R^8$ is independently a C1-10 alkyl or aryl group optionally containing at least one heteroatom. In one embodiment, $R^8$ is a methyl group (Me).

The catalyst utilized in the process of the present invention is illustrated in Formula (I) above wherein Co is in any valence or oxidation state (e.g., +1, +2, or +3). In one embodiment, at least one of $R^6$ and $R^7$ is a C1-C10 alkyl. Examples of suitable groups for $R^6$ and $R^7$ include, but are not limited to, methyl, ethyl, propyl, butyl, or cyclohexyl, etc. Non-limiting examples of suitable compounds include:

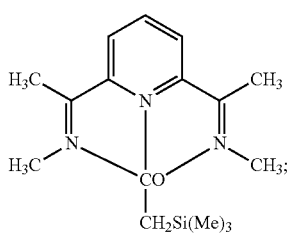

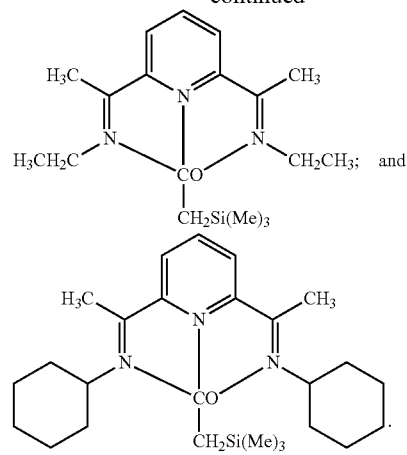

Various methods can be used to prepare the catalyst utilized in the process of the present invention. In one embodiment, the catalyst is generated in-situ by contacting a catalyst precursor with an activator in the presence of a liquid medium containing at least one component selected from the group consisting of a solvent, the silyl hydride, the compound containing at least one unsaturated group, and combinations thereof, wherein the catalyst precursor is represented by structural Formula II (II)

wherein each occurrence of $R^1$, $R^2$, $R^3$, $R^4$, and $R^5$ is independently hydrogen, C1-C18 alkyl, C1-C18 substituted alkyl, aryl, substituted aryl, or an inert substituent, wherein $R^1$-$R^5$, other than hydrogen, optionally contain at least one heteroatom;

each occurrence of $R^6$ and $R^7$ is independently C1-C18 alkyl, C1-C18 substituted alkyl, aryl or substituted aryl, wherein $R^6$ and $R^7$ optionally contain at least one heteroatom;

optionally any two of $R^1$, $R^2$, $R^3$, $R^4$, $R^5$, $R^6$ and $R^7$ vicinal to one another taken together may form a ring being a substituted or unsubstituted, saturated, or unsaturated cyclic structure; and X is an anion selected from the group consisting of $F^-$, $Cl^-$, $Br^-$, $I^-$, $CF_3R^{40}SO_3^-$ or $R^{50}COO^-$, wherein $R^{40}$ is a covalent bond or a C1-C6 alkylene group, and $R^{50}$ is a C1-C10 hydrocarbyl group.

The activator is an alkali metal alkyl of the formula $MCH_2SiR^8_3$, where M is an alkali metal.

The methods to prepare the catalysts are known to a person skilled in the field. For example, the catalysts can be prepared by reacting a PDI ligand with a metal halide, such as $CoCl_2$ as disclosed in US Patent Application Publication 2011/0009573A1. Typically, the PDI ligands are produced through condensation of an appropriate amine or aniline with 2,6- diacetylpyridine and its derivatives. If desired, the PDI ligands can be further modified by known aromatic substitution chemistry.

In the process of the invention, the catalysts can be unsupported or immobilized on a support material, for example, carbon, silica, alumina, MgCl$_2$ or zirconia, or on a polymer or prepolymer, for example polyethylene, polypropylene, polystyrene, poly(aminostyrene), or sulfonated polystyrene. The metal complexes can also be supported on dendrimers.

In some embodiments, for the purposes of attaching the metal complexes of the invention to a support, it is desirable that at least one of $R^1$ to $R^9$ of the metal complexes, preferably $R^6$, has a functional group that is effective to covalently bond to the support. Exemplary functional groups include but are not limited to SH, COOH, NH$_2$ or OH groups.

In one embodiment, silica supported catalyst may be prepared via Ring-Opening Metathesis Polymerization (ROMP) technology as discussed in the literature, for example Macromol. Chem. Phys. 2001, 202, No. 5, pages 645-653; Journal of Chromatography A, 1025 (2003) 65-71.

One way to immobilize catalysts on the surface of dendrimers is by the reaction of Si—Cl bonded parent dendrimers and functionalized PDI in the presence of a base is as illustrated by Kim et al. in Journal of Organometallic Chemistry 673 (2003) 77-83.

The unsaturated compound containing at least one unsaturated functional group utilized in the process of the invention can be a compound having one, two, three, or more unsaturations. Examples of such unsaturated compounds include an olefin, a cycloalkene, unsaturated polyethers such as an alkyl-capped allyl polyether, a vinyl-functional alkyl-capped allyl or methallyl polyether, an alkyl-capped terminally unsaturated amine, an alkyne, terminally unsaturated acrylate or methacrylate, unsaturated aryl ether, vinyl-functionalized polymer or oligomer, vinyl-functionalized silane, vinyl-functionalized silicone, unsaturated fatty acids, unsaturated esters, and combinations thereof.

Unsaturated polyethers suitable for the dehydrogenative silylation reaction preferably are polyoxyalkylenes having the general formula:

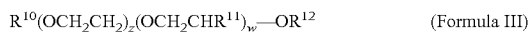

$R^{10}(OCH_2CH_2)_z(OCH_2CHR^{11})_w$—$OR^{12}$ (Formula III)

or

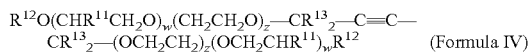

$R^{12}O(CHR^{11}CH_2O)_w(CH_2CH_2O)_z$—$CR^{13}_2$—C≡C—$CR^{13}_2$—$(OCH_2CH_2)_z(OCH_2CHR^{11})_wR^{12}$ (Formula IV)

or

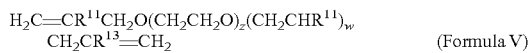

$H_2C$=$CR^{11}CH_2O(CH_2CH_2O)_z(CH_2CHR^{11})_w$
$CH_2CR^{13}$=$CH_2$ (Formula V)

wherein $R^{10}$ denotes an unsaturated organic group containing from 2 to 10 carbon atoms such as allyl, methylallyl, propargyl or 3-pentynyl. When the unsaturation is olefinic, it is desirably terminal to facilitate smooth dehydrogenative silylation and/or hydrosilylation. However, when the unsaturation is a triple bond, it may be internal. $R^{12}$ is hydrogen, vinyl, or a polyether capping group of from 1 to 8 carbon atoms such as the alkyl groups: CH$_3$, n-C$_4$H$_9$, t-C$_4$H$_9$ or i-C$_8$H$_{17}$, the acyl groups such as CH$_3$COO, t-C$_4$H$_9$COO, the beta-ketoester group such as CH$_3$C(O)CH$_2$C(O)O, or a trialkylsilyl group. $R^{11}$ and $R^{13}$ are monovalent hydrocarbon groups such as the C1-C20 alkyl groups, for example, methyl, ethyl, isopropyl, 2-ethylhexyl, dodecyl and stearyl, or the aryl groups, for example, phenyl and naphthyl, or the alkaryl or aralkyl groups, for example, benzyl, phenylethyl and nonylphenyl, or the cycloalkyl groups, for example, cyclohexyl and cyclooctyl. $R^{13}$ may also be hydrogen. Methyl is the most preferred $R^{11}$ and $R^{13}$ groups. Each occurrence of z is 0 to 100 inclusive and each occurrence of w is 0 to 100 inclusive. Preferred values of z and w are 1 to 50 inclusive.

Specific examples of preferred unsaturated compounds useful in the process of the present invention include N,N-dimethylallyl amine, allyloxy-substituted polyethers, propylene, 1-butene, 1-hexene, styrene, vinylnorbornane, 5-vinylnorbornene, long-chain, linear alpha olefins such as 1-octadecene, internal olefins such as cyclopentene, cyclohexene, norbornene, and 3-hexene, branched olefins such as isobutylene and 3-methyl-1-octene, unsaturated polyolefins, e.g., polybutadiene, polyisoprene and EPDM, unsaturated acids or esters such as oleic acid, linoleic acid and methyl oleate, a vinyl siloxane of the Formula VI and combinations thereof, wherein Formula VI is

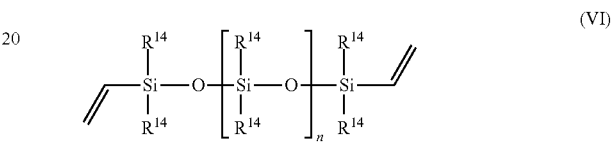

(VI)

wherein each occurrence of $R^{14}$ is independently a C1-C18 alkyl, C1-C18 substituted alkyl, vinyl, aryl, or a substituted aryl, and n is greater than or equal to zero. In one embodiment, n is 0-500, 1-250, 50-150, etc. Here, as elsewhere in the specification and claims, numerical values may be combined to form new and non-disclosed ranges. As defined herein, "internal olefin" means an olefin group not located at a chain or branch terminus, such as 3-hexene.

The silyl hydride employed in the reaction is not particularly limited. It can be any compound selected from the group consisting of $R_aSiH_{4-a}$, $(RO)_aSiH_{4-a}$, $Q_uT_vT_p^HD_wD^H_xM^H_yM_z$, and combinations thereof. The silyl hydride can contain linear, branched or cyclic structures, or combinations thereof. As used herein, each occurrence of R is independently C1-C18 alkyl, C1-C18 substituted alkyl, wherein R optionally contains at least one heteroatom, each occurrence of a independently has a value from 0 to 3, each of p, u, v, y and z independently has a value from 0 to 20, w and x are from 0 to 500, provided that p+x+y equals 1 to 500 and the valences of the all the elements in the silyl hydride are satisfied. Preferably, p, u, v, y, and z are from 0 to 10, w and x are from 0 to 100, wherein p+x+y equals 1 to 100.

As used herein, an "M" group represents a monofunctional group of formula $R'_3SiO_{1/2}$, a "D" group represents a difunctional group of formula $R'_2SiO_{2/2}$, a "T" group represents a trifunctional group of formula $R'SiO_{3/2}$, and a "Q" group represents a tetrafunctional group of formula $SiO_{4/2}$, an "$M^H$" group represents $HR'_2SiO_{1/2}$, a "$T^H$" represents $HSiO_{3/2}$, and a "$D^H$" group represents $R'HSiO_{2/2}$. Each occurrence of R' is independently C1-C18 alkyl, C1-C18 substituted alkyl, wherein R' optionally contains at least one heteroatom.

Examples of silyl hydrides containing at least one silylhydride functional group include $R_aSiH_{4-a}$, $(RO)_aSiH_{4-a}$, $HSiH_a(OR)_{3-a}$, $R_3Si(CH_2)_f(SiR_2O)_kSiR_2H$, $(RO)_3Si(CH_2)_f(SiR_2O)_kSiR_2H$, $Q_uT_vT_p^HD_wD^H_xM^H_yM_z$, and combinations thereof, wherein Q is $SiO_{4/2}$, T is $R'SiO_{3/2}$, $T^H$ is $HSiO_{3/2}$, D is $R'_2SiO_{2/2}$, $D^H$ is $R'HSiO_{2/2}$, $M^H$ is $HR'_2SiO_{1/2}$, M is $R'_3SiO_{1/2}$, each occurrence of R and R' is independently C1-C18 alkyl, C1-C18 substituted alkyl, aryl, or substituted aryl, wherein R and R' optionally contain at least one heteroatom, each occurrence of a independently has a value from 1 to 3 (with the proviso that the silicon remains tetravalent), f has a value of 1 to 8, k has a value of 1 to 11, g has a value of from 1 to 3, p is from 0 to 20, u is from 0 to 20, v is from 0 to 20, w is from 0 to 1000, x is from 0 to 1000, y is from 0 to 20, and z is from 0 to 20, provided that p+x+y equals 1 to 3000, and the valences of the all the elements in the silyl hydride are satisfied. In the above formulations, p, u, v, y, and z may also be from 0 to 10, w and x may be from 0 to 100, wherein p+x+y equals 1 to 100.

The instant invention also provides hydrosilylation with hydridosiloxanes comprising carbosiloxane linkages (for example, Si—CH$_2$—Si—O—SiH, Si—CH$_2$—CH$_2$—Si—O—SiH or Si-arylene-Si—O—SiH). Carbosiloxanes contain both the —Si-(hydrocarbylene)-Si— and —Si—O—Si— functionalities, where hydrocarbylene represents a substituted or unsubstituted, divalent alkylene, cycloalkylene or arylene group. The synthesis of carbosiloxanes is disclosed in U.S. Pat. No. 7,259,220; U.S. Pat. No. 7,326,761 and U.S. Pat. No. 7,507,775 all of which are incorporated herein in their entirety by reference. An exemplary formula for hydridosiloxanes with carbosiloxane linkages is $R_3Si(CH_2R)_x SiOSiR_2(OSiR_2)_y OSiR_2H$, wherein each occurrence of R is independently a monovalent alkyl, cycloalkyl or aryl group. In one embodiment, R is independently C1-C18 alkyl, C1-C18 substituted alkyl, aryl, or substituted aryl. In one embodiment, R is chosen from methyl, ethyl, cyclohexyl or phenyl. Additionally, R in the hydridosiloxane with carbosiloxane linkages, independently may also be H. The subscript x has a value of 1-8, y has a value from zero to 10 and is preferably zero to 4. A specific example of a hydridocarbosiloxane is $(CH_3)_3SiCH_2CH_2Si(CH_3)_2OSi(CH_3)_2H$.

In one embodiment, the silyl hydride has one of the following structures:

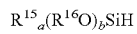  (Formula VII)

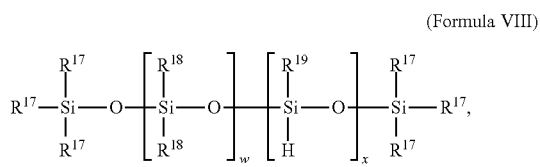  (Formula VIII)

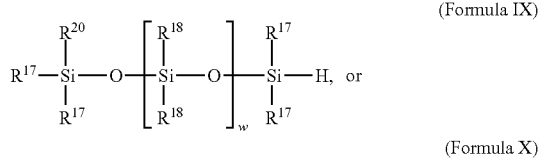  (Formula IX)

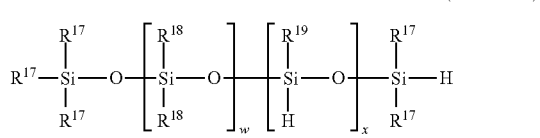  (Formula X)

wherein each occurrence of $R^{15}$, $R^{16}$, $R^{17}$, $R^{18}$, and $R^{19}$ is independently a C1-C18 alkyl, C1-C18 substituted alkyl, aryl, or substituted aryl, $R^{20}$ is hydrogen, a C1-C18 alkyl, C1-C18 substituted alkyl, aryl, or substituted aryl, x and w are independently greater than or equal to 0 (x is at least equal to 1 for Formula VIII)), and a and b are integers from 0 to 3 provided that a+b=3.

Effective catalyst usage for dehydrogenative silylation ranges from 0.01 mole percent to 10 mole percent based on the molar quantity of the alkene to be reacted. In one embodiment, the catalyst level is 0.01 mole percent to 10 mole percent, 0.05 mole percent to 7.5 mole percent, 0.1 to 5 mole percent, 0.5 to 2.5 mole percent, even 1 to 2 mole percent. Reaction may be run at temperatures from about 0° C. up to 300° C., depending on the thermal stability of the alkene, silyl hydride and the specific pyridine diimine complex. Temperatures in the range, 20-100° C., have been found to effective for most reactions. Heating of reaction mixtures can be done using conventional methods as well as with microwave devices.

The dehydrogenative silylation and/or hydrosilylation reactions of this invention can be run at subatmospheric and suprastmospheric pressures. Typically, pressures from about 1 atmosphere (0.1 MPa) to about 200 atmospheres (20 MPa), preferably to about 50 atmospheres (5.0 MPa), are suitable. Higher pressures are effective with volatile and/or less reactive alkenes which require confinement to enable high conversions.

A variety of reactors can be used in the process of this invention. Selection is determined by factors such as the volatility of the reagents and products. Continuously stirred batch reactors are conveniently used when the reagents are liquid at ambient and reaction temperature. These reactors can also be operated with a continuous input of reagents and continuous withdrawal of dehydrogenatively silylated reaction product.

With gaseous or volatile olefins and silanes, fluidized-bed reactors, fixed-bed reactors and autoclave reactors can be more appropriate. Alternatively, the cobalt pyridinediimine catalyst can be placed in an autoclave reactor, or supported in a catalyst basket therein, and the reagents charged and maintained at the selected temperature and pressure to effect the dehydrogenative silylation and/or hydrosilylation.

The catalysts of the invention are useful for catalyzing dehydrogenative silylation and/or hydrosilylation reactions. An example is shown in the reaction scheme below.

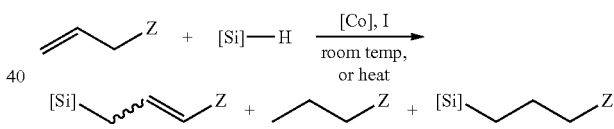

The reactions are typically facile at ambient temperatures and pressures, but can also be run at lower or higher temperatures (0 to 300° C.) or pressures (ambient to 205 atmospheres, (0.1-20.5 MPa)). A range of unsaturated compounds can be used in this reaction, such as N,N-dimethylallyl amine, allyloxy-substituted polyethers, cyclohexene, and linear alpha olefins (i.e., 1-butene, 1-octene, 1-dodecene, etc.).

Because the double bond of an alkene is preserved during the dehydrogenative silylation reaction employing these cobalt catalysts, a singly-unsaturated olefin may be used to crosslink silyl-hydride containing polymers. Alternatively, an unsaturated siloxane polymer may be used in a hydrosilylation reaction to produce a cross-linked product. A variety of new materials can be produced by this method by varying the hydride polymer and length of the olefin used for the crosslinking. Accordingly, the catalysts used in the process of the invention have utility in the preparation of useful silicone products, including, but not limited to, coatings, for example release coatings, room temperature vulcanizates, sealants, adhesives, products for agricultural and personal care applications, and silicone surfactants for stabilizing polyurethane foams.

Furthermore, the dehydrogenative silylation and/or hydrosilylation may be carried out on any of a number of unsaturated polyolefins, such as polybutadiene, polyisoprene or EPDM-type copolymers, to either functionalize these commercially important polymers with silyl groups or crosslink them via the use of hydrosiloxanes containing multiple SiH groups at lower temperatures than conventionally used. This offers the potential to extend the application of these already valuable materials in newer commercially useful areas.

In one embodiment, the catalysts are useful for dehydrogenative silylation and/or hydrosilylation of a composition containing a silyl hydride and a compound having at least one unsaturated group. The process includes contacting the composition with a metal complex of the catalyst, either supported or unsupported, to cause the silyl hydride to react with the compound having at least one unsaturated group to produce a dehydrogenative silylation and/or hydrosilylation product, which may contain the metal complex catalyst. The dehydrogenative silylation and/or hydrosilylation reaction can be conducted optionally in the presence of a solvent. If desired, when the dehydrogenative silylation and/or hydrosilylation reaction is completed, the metal complex can be removed from the reaction product by magnetic separation and/or filtration. These reactions may be performed neat, or diluted in an appropriate solvent. Typical solvents include benzene, toluene, diethyl ether, etc. It is preferred that the reaction is performed under an inert atmosphere. The catalyst can be generated in-situ by reduction using an appropriate reducing agent.

The manner or order in which the respective components for carrying out the process are added to one another is not particularly limited and can be chosen as desired. In one embodiment, the silylhydride can be added to a mixture containing the metal complex and the unsaturated olefin. In another embodiment, the unsaturated olefin can be added to a mixture containing the metal complex and the silylhydride. In still another embodiment, a mixture of silylhydride and unsaturated olefin can be added to a mixture of metal complex, silylhydride and unsaturated olefin. It will be appreciated that the first mixtures in the above embodiments may be heated or preliminarily reacted prior to addition of the remaining components.

The catalyst complexes of the invention are efficient and selective in catalyzing dehydrogenative silylation and/or hydrosilylation reactions. For example, when the catalyst complexes of the invention are employed in the dehydrogenative silylation and/or hydrosilylation of an alkyl-capped allyl polyether or a compound containing an unsaturated group, the reaction products are essentially free of unreacted alkyl-capped allyl polyether and its isomerization products. In one embodiment, the reaction products do not contain the unreacted alkyl-capped allyl polyether and its isomerization products. Further, when the compound containing an unsaturated group is an unsaturated amine compound, the dehydrogenatively silylated and/or hydrosilylated product is essentially free of internal addition products and isomerization products of the unsaturated amine compound. As used herein, "essentially free" is meant no more than 10 wt %, preferably 5 wt % based on the total weight of the hydrosilylation product. "Essentially free of internal addition products" is meant that silicon is added to the terminal carbon.

The following examples are intended to illustrate, but in no way limit the scope of the present invention. All parts and percentages are by weight and all temperatures are in degrees Celsius unless explicitly stated otherwise. All the publications and the US patents referred to in the application are hereby incorporated by reference in their entireties.

EXAMPLES

General Considerations

All air- and moisture-sensitive manipulations were carried out using standard vacuum line, Schlenk (Argon), and cannula techniques or in an MBraun inert atmosphere dry box containing an atmosphere of purified nitrogen. Solvents for air- and moisture-sensitive manipulations were initially dried and deoxygenated using literature procedures described in Pangborn, A. B.; Giardello, M. A.; Grubbs, R. H.; Rosen, R. K.; Timmers, F. J. *Organometallics* 1996, 15, 1518. SilForce® SL6100 ($M^{vi}D_{120}M^{vi}$), SilForce® SL6020 ($MD_{15}D^{H}_{30}M$) were acquired from Momentive Performance Materials and dried under high vacuum for 12 hours before use.

All silanes and alkene substrates are dried over $CaH_2$ or $LiAlH_4$, then distilled under vacuum and stored under $N_2$. $^1H$ NMR spectra were recorded on Bruker AVANCE 300, Varian Inova 400 and Bruker AVANCE 500 spectrometers operating at 300.13, 399.78, and 500.62 MHz, respectively. $^{13}C$ NMR spectra were either recorded on a Bruker 500 spectrometer operating at 125.853 MHz. All $^1H$ and $^{13}C$ NMR chemical shifts are reported relative to $SiMe_4$ using the $^1H$ (residual) and $^{13}C$ chemical shifts of the solvent as a secondary standard. GC analyses were performed using a Shimadzu GC-2010 gas chromatograph equipped with a Shimadzu AOC-20s autosampler and a Shimadzu SHRXI-5MS capillary column (15m×250 μm). The instrument was set to an injection volume of 1 μL, an inlet split ratio of 20:1, and inlet and detector temperatures of 250° C. and 275° C., respectively. UHP-grade helium was used as carrier gas with a flow rate of 1.82 mL/min. The temperature program used for all the analyses is as follows: 60° C., 1 min; 15° C./min to 250° C., 2 min.

Catalyst loadings in the following text are reported in mol % of the cobalt complex($mol_{Co\ complex}$/$mol_{olefin}$×100).

Attempted Synthesis of $^{Me}$APDICoMe

This procedure is based upon that used for the synthesis of $^{Me}$APDICoNs (vide supra) In a nitrogen-filled drybox, a scintillation vial was charged with 0.078 g (0.244 mmol) of $^{Me}$APDICoCl$_2$ and approximately 8 mL of THF. The suspension was chilled at −35° C. for 20 minutes. To this suspension was then added dropwise a diethyl ether solution of methyllithium (1.60 M in diethyl ether, 0.306 mL), during which time a solution color change to black with concomitant formation of dark precipitate was observed. The reaction mixture was stirred at room temperature for 3 hours, after which the volatiles were removed in vacuo. The residue contained a complex mixture of unidentified cobalt-containing products. Notably no evidence for the formation of the expected $^{Me}$APDICoMe was found.

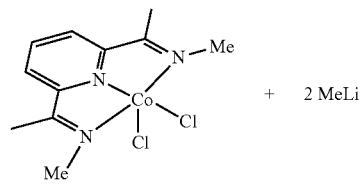

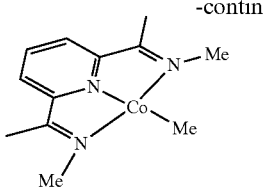

Example 1

Synthesis of $^{Me}$APDICoNs

In a nitrogen-filled drybox, a scintillation vial was charged with 0.350 g (1.097 mmol) of $^{Me}$APDICoCl$_2$ and approximately 14 mL of THF. The suspension was chilled at −35° C. for 20 minutes. To this suspension was then added dropwise a THF solution of (trimethylsilyl)methyllithium (0.207 g in 3 mL THF), during which time a solution color change to purple was observed. The reaction mixture was stirred at room temperature overnight, after which the volatiles were removed in vacuo. The residue was extracted with diethyl ether, filtered through Celite, and concentrated. Layering the supernatant with pentane and recrystallization at −35° C. yielded 0.155 g (42%) of a purple solid identified as $^{Me}$APDICoNs. $^1$H NMR (benzene-d$_6$, 23° C.): δ=9.83 (t, 8 Hz, 1H), 7.21 (d, 8 Hz, 2H), 3.98 (s, 6H), 1.22 (s, 2H), −0.11 (s, 9H), −0.57 (s, 6H). $^{13}$C NMR (benzene-d$_6$, 23° C.): δ=165.29, 152.49, 122.43, 114.04, 48.25, 30.25, 20.95, 3.39.

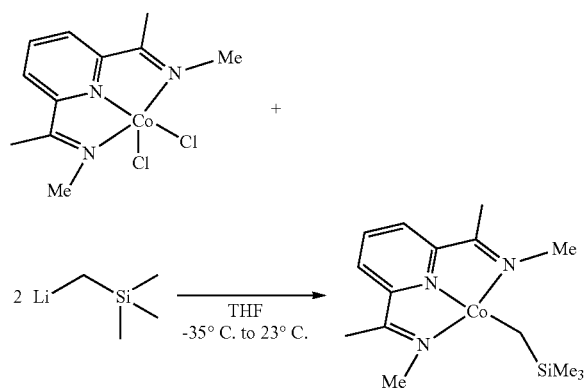

Example 2

Synthesis of $^{Et}$APDICoNs

In a nitrogen-filled drybox, a scintillation vial was charged with 0.134 g (0.386 mmol) of $^{Et}$APDICoCl$_2$ and approximately 10 mL of THF. The suspension was chilled at −35° C. for 20 minutes. To this suspension was then added dropwise a THF solution of (trimethylsilyl)methyllithium (0.073 g in 1 mL THF), during which time a solution color change to purple was observed. The reaction mixture was stirred at room temperature overnight, after which the volatiles were removed in vacuo. The residue was extracted with toluene, filtered through Celite, and concentrated. Layering the supernatant with pentane and recrystallization at −35° C. yielded 0.093 g (66.3%) of a purple solid identified as $^{Et}$APDICoNs. $^1$H NMR (benzene-d$_6$, 23° C.): δ=9.80 (t, 8 Hz, 1H), 7.28 (d, 8 Hz, 2H), 5.21 (q, 7 Hz, 4H), 1.70 (t, 7 Hz, 6H), 1.17 (s, 2H), −0.13 (s, 9H), −0.37 (s, 6H). $^{13}$C NMR (benzene-d$_6$, 23° C.): δ=162.77, 152.73, 122.55, 114.03, 53.59, 20.29, 12.52, 3.31, 0.05.

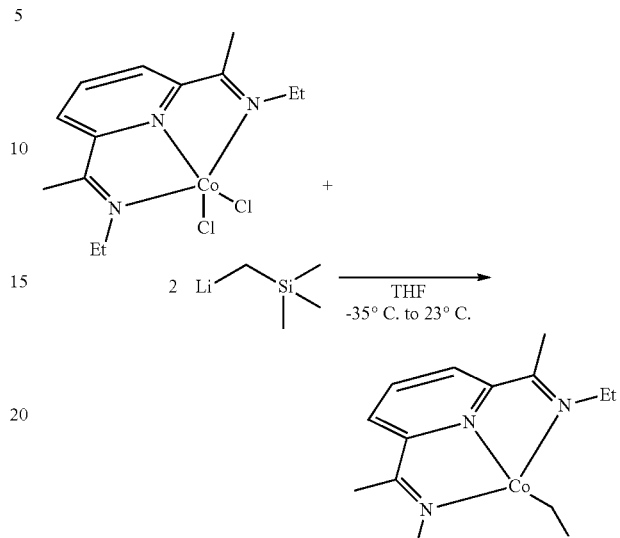

Example 3

Synthesis of $^{Cy}$APDICoNs

In a nitrogen-filled drybox, a scintillation vial was charged with 0.280 g (0.667 mmol) of $^{Cy}$APDICoCl (Bowman, A. C.; Milsmann, C.; Bill, E.; Lobkovsky, E.; Weyhermüller, T.; Wieghardt, K.; Chirik P. J. *Inorg. Chem.* 2010, 49, 6110-6123) and approximately 14 mL of diethyl ether. The suspension was chilled at −35° C. for 20 minutes. To this suspension was then added dropwise a diethyl ether solution of (trimethylsilyl)methyllithium (0.066 g in 3 mL diethylether), during which time a solution color change from orange to purple was observed. The reaction mixture was stirred at room temperature for 1 hour, after which time the mixture was filtered through Celite, and concentrated. Layering the supernatant with pentane and recrystallization at −35° C. yielded 0.250 g (79%) of a purple solid identified as $^{Cy}$APDICoNs. $^1$H NMR (benzene-d$_6$, 23° C.): δ=9.68 (t, 8 Hz, 1H), 7.43 (d, 8 Hz, 2H), 6.93 (br, 2H), 4.27 (m, 2H), 3.15-1.18 (m, 20H), −0.01 (s, 6H), −0.45 (s, 9H). $^{13}$C NMR (benzene-d$_6$, 23° C.): δ=158.84, 144.50, 128.13, 109.13, 70.56, 26.23, 25.99, 21.49, 2.18.

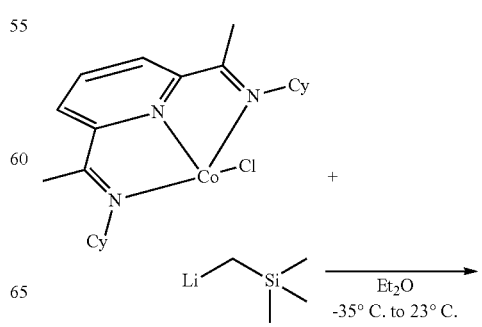

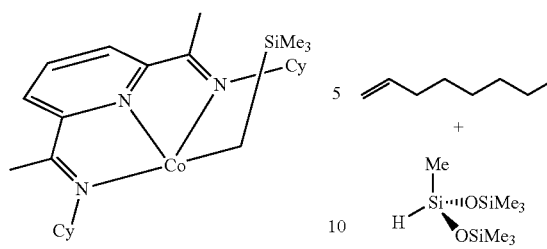

Examples 4-6

General Procedure for the Silylation of 1-Octene with Different Silanes Using $^{Cy}$APDICoNs In a nitrogen-filled drybox, a scintillation vial was charged with 0.100 g (0.891 mmol) of 1-octene and 0.002 g (0.004 mmol) $^{Cy}$APDICoNs (0.5 mol %), 0.891 mmol of silane (0.146 g (EtO)$_3$SiH, 0.198 g of MD$^H$M or 0.104 g of Et$_3$SiH) was then added to the mixture and the reaction was stirred at room temperature for desired amount of time. The product mixture was quenched by exposure to air. The product mixture was filtered through a plug of silica gel (Fluka® high-purity grade, pore size 60, 230-400 mesh particle size, 40-63 μm particle size, for flash chromatography) and eluted with hexane. The crude product mixture was analyzed by GC. Volatiles were then removed from the crude mixture product and the resulting mixture was analyzed by $^1$H and $^{13}$C NMR spectroscopy.

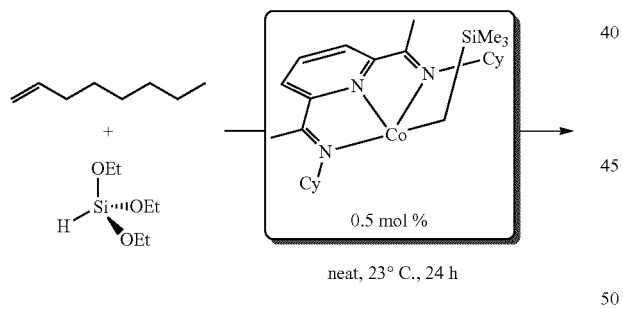

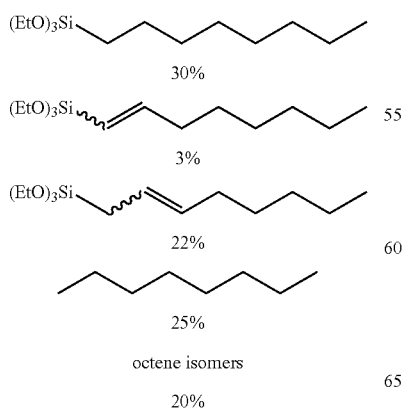

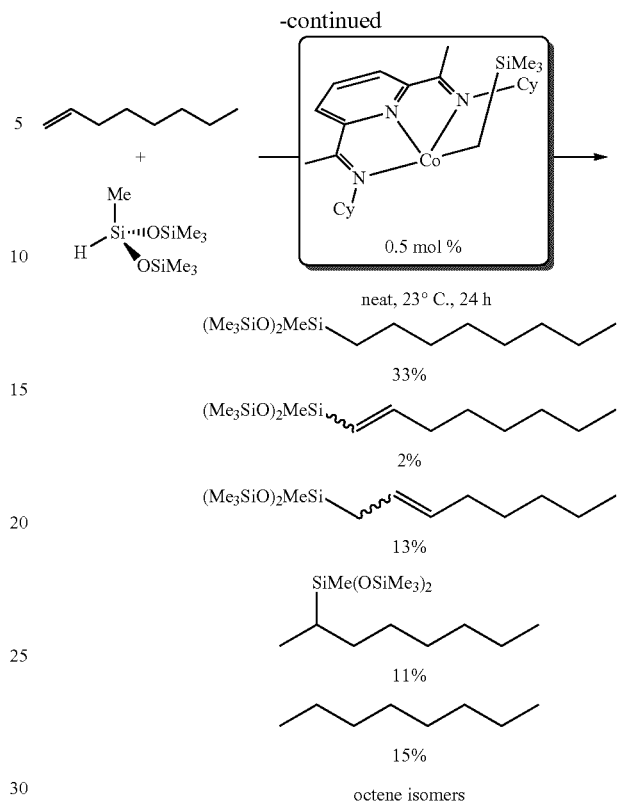

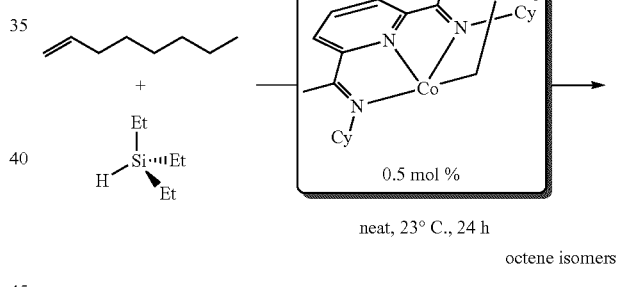

Examples 7-9

General Procedure for the Silylation of 1-Octene with Different Silanes Using $^{Et}$APDICoNs In a nitrogen-filled drybox, a scintillation vial was charged with 0.100 g (0.891 mmol) of 1-octene and 0.002 g (0.004 mmol) $^{Et}$APDICoNs (0.5 mol %), 0.891 mmol of silane (0.146 g (EtO)$_3$SiH, 0.198 g of MD$^H$M or 0.104 g of Et$_3$SiH) was then added to the mixture and the reaction was stirred at room temperature for desired amount of time. The product mixture was quenched by exposure to air. The product mixture was filtered through silica gel and eluted with hexane. The product mixture was directly injected to GC. The resulting solution was dried under vacuum and the remaining residue was analyzed by $^1$H and $^{13}$C NMR spectroscopy. The yields are based on conversion of 1-octene.

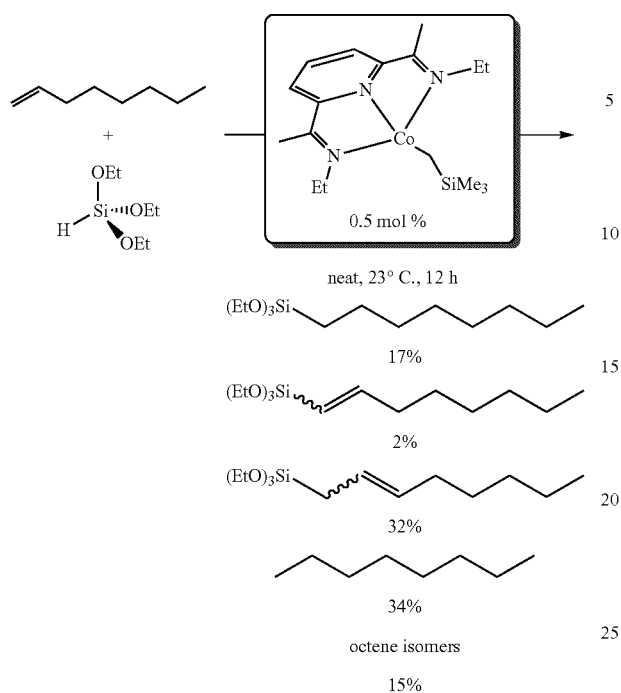

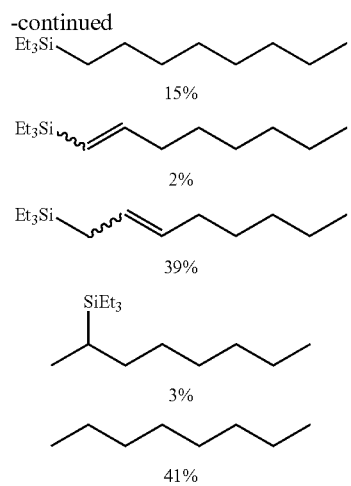

Examples 10-12

General Procedure for the Silylation of 1-Octene with Different Silanes Using $^{Me}$APDICoNs In a nitrogen-filled drybox, a scintillation vial was charged with 0.100 g (0.891 mmol) of 1-octene and approximately 0.001 g (0.004 mmol) $^{Me}$APDICoNs (0.5 mol %), 0.891 mmol of silane (0.146 g (EtO)$_3$SiH, 0.198 g of MD$^H$M or 0.104 g of Et$_3$SiH) was then added to the mixture and the reaction was stirred at room temperature for desired amount of time. The product mixture was quenched by exposure to air. The product mixture was filtered through silica gel and eluted with hexane. The product mixture was directly injected to GC. The resulting solution was dried under vacuum and the remaining residue was analyzed by $^1$H and $^{13}$C NMR spectroscopy. The yields are based on conversion of 1-octene.

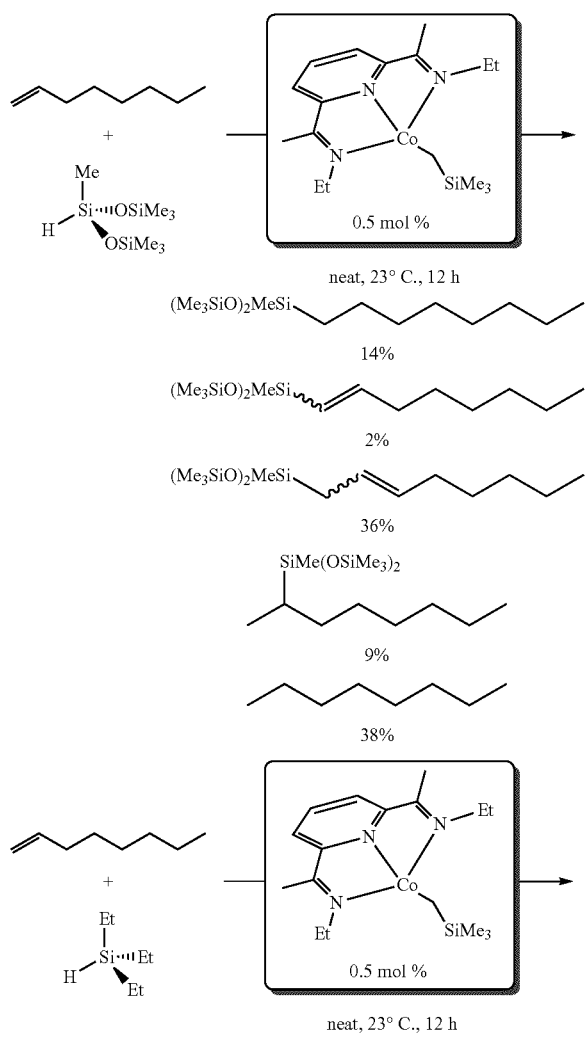

were then removed from the crude mixture product and the resulting mixture was analyzed by $^1$H and $^{13}$C NMR spectroscopy.

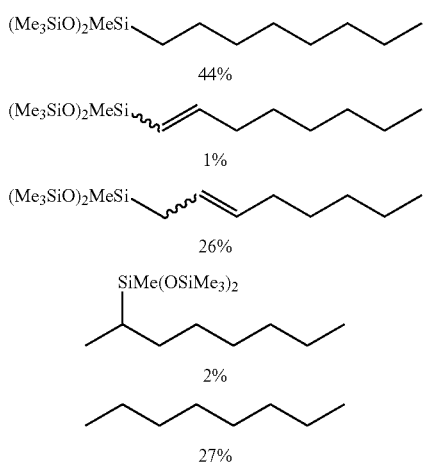

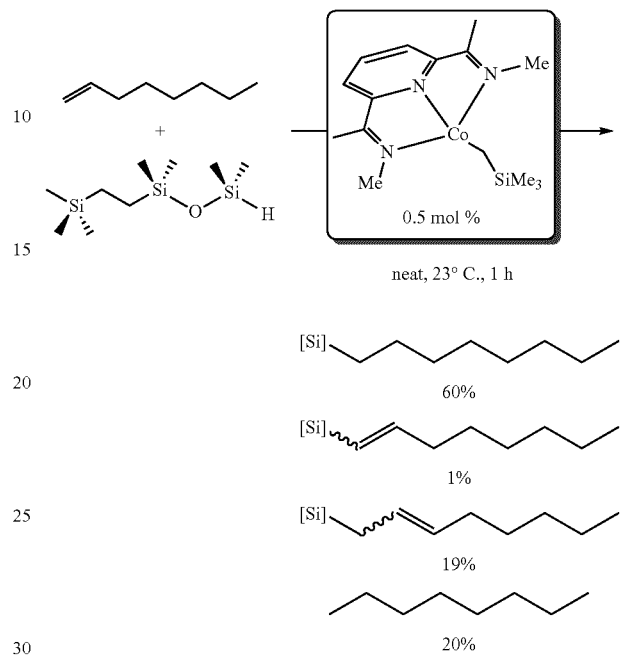

Example 13

Silylation of 1-octene with 1-(2-trimethylsilylethyl)-1,1,3,3-tetramethyldisiloxane using $^{Me}$APDICoNs In a nitrogen-filled drybox, a scintillation vial was charged with 0.100 g (0.891 mmol) of 1-octene and approximately 0.001 g (0.004 mmol) $^{Me}$APDICoNs (0.5 mol %). 1-(2-trimethylsilylethyl)-1,1,3,3-tetramethyldisiloxane (0.209 g, 0.891 mmol) was then added to the mixture and the reaction was stirred at room temperature for 1 hour, after which the mixture was quenched by exposure to air. The product mixture was filtered through silica gel and eluted with hexane. The crude product mixture was analyzed by GC. Volatiles

Example 14

Silylation of 1-octene with 2-(trimethylsilyl)ethyldimethylsilane using $^{Me}$APDICoNs In a nitrogen-filled drybox, a scintillation vial was charged with 0.100 g (0.891 mmol) of 1-octene and approximately 0.001 g (0.004 mmol) $^{Me}$APDICoNs (0.5 mol %). 2-(trimethylsilyl)ethyldimethylsilane (0.143 g, 0.891 mmol) was then added to the mixture and the reaction was stirred at room temperature for 1 hour, after which the mixture was quenched by exposure to air. The product mixture was filtered through silica gel and eluted with hexane. The crude product mixture was analyzed by GC. Volatiles were then removed from the crude product mixture and the residue was analyzed by $^1$H and $^{13}$C NMR spectroscopy.

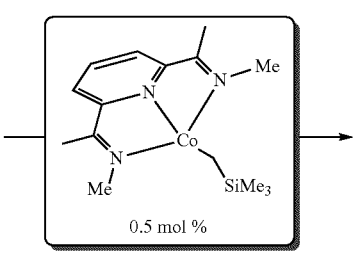

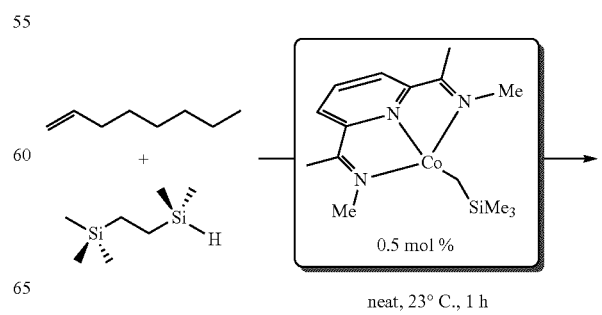

Example 15

Catalytic Hydrosilylation of 1-Octene with (EtO)₃SiH at Low $^{Me}$APDICoNs Loading

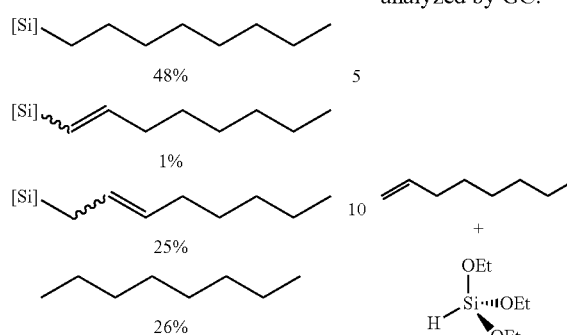

In a nitrogen-filled drybox, a scintillation vial was charged with 0.400 g (3.56 mmol) of 1-octene and 100 μL of a 16 mM toluene solution of $^{Me}$APDICoNs. Then to the mixture was added 0.586 g of (EtO)₃SiH dropwise over a period of 20 seconds and the resulting reaction mixture was stirred at room temperature for 80 minutes. The product mixture was quenched by exposure to air. The product mixture was filtered through silica gel and eluted with hexane. The product mixture was analyzed by GC.

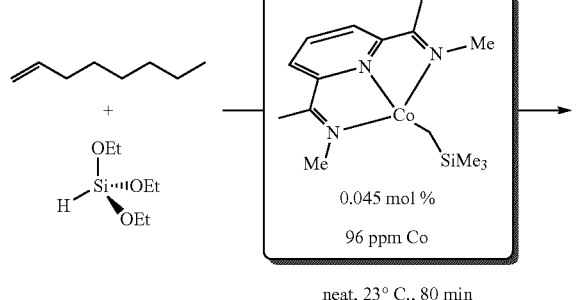

Example 16

Catalytic hydrosilylation of 1-octene with (EtO)₃SiH at elevated temperature using $^{Me}$APDICoNs In a nitrogen-filled drybox, a scintillation vial was charged with 0.400 g (3.56 mmol) of 1-octene and 200 μL of a 4 mM toluene solution of $^{Me}$APDICoNs. Then to the mixture was added 0.586 g of (EtO)₃SiH dropwise over a period of 20 seconds and the resulting reaction mixture was stirred at 60° C. for 3 hours. The product mixture was quenched by exposure to air. The product mixture was filtered through silica gel and eluted with hexane. The product mixture was analyzed by GC.

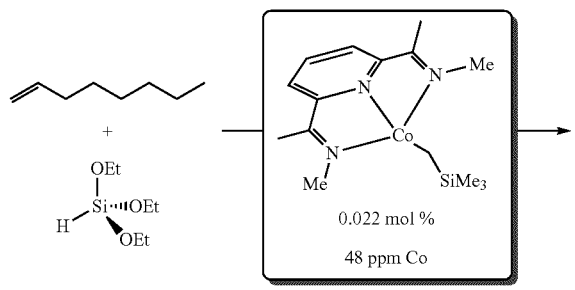

Example 17

Cross-Linking Using Momentive SL6100 and SL6020 D1 Using $^{Me}$APDICoNs

In a nitrogen-filled drybox, a scintillation vial was charged with 3.000 g of mixture of $M^{vi}D_{120}M^{vi}$ (SL6100) and $MD_{15}D^H_{30}M$ (SL6020) (in 1:2 molar ratio). Then to the mixture was added 20 μL of a 4 mM toluene solution of $^{Me}$APDICoNs (10 ppm Co). The reaction mixture was then stirred at room temperature. Complete gelation was achieved in 1 hour. When the reaction was performed at 80° C., complete gelation occurred within 1 minute.

Example 18

Silylation of 1-Octene with Momentive SL6020 D1 Using $^{Me}$APDICoNs

In a nitrogen-filled drybox, a scintillation vial was charged with 0.100 g (0.891 mmol) of 1-octene, 0.500 g benzene and approximately 0.001 g (0.004 mmol) $^{Me}$APDICoNs, $MD_{15}D^H_{30}M$ (0.091 g) was then added and the reaction mixture was stirred at room temperature for 1 hour. The product mixture was quenched by exposure to air. The product mixture was filtered through silica gel and eluted with hexane. The product mixture was analyzed by ¹H NMR spectroscopy. The ¹H NMR (benzene-d₆) spectrum of the product mixture revealed vinyl proton signals at 5.5-6.0 ppm, characteristic of dehydrogenative silylation.

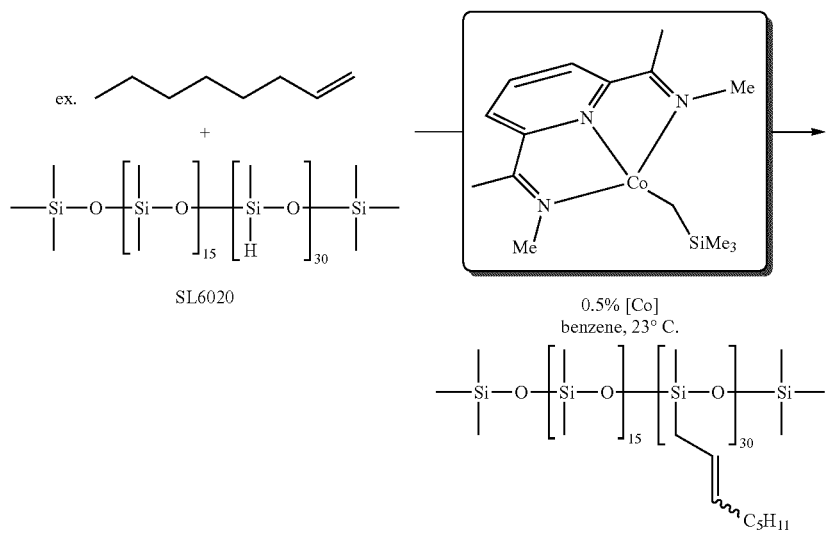

Example 19

Silylation of Momentive SL6100 with (EtO)₃SiH Using $^{Me}$APDICoNs

In a nitrogen-filled drybox, a scintillation vial was charged with 1.000 g of M$^{vi}$D$_{120}$M$^{vi}$ (SL6100), 0.500 g benzene and approximately 0.001 g (0.004 mmol) $^{Me}$APDICoNs, MD$^H$M (0.200 g, 0.891 mmol) was then added and the reaction mixture was stirred at room temperature for 1 hour. The product mixture was quenched by exposure to air. The product mixture was filtered through silica gel and eluted with hexane. The product mixture was analyzed by $^1$H NMR spectroscopy. The $^1$H NMR (benzene-d₆) spectrum of the product mixture contained no vinyl proton signals, signaling hydrosilylation products. The products were identified as a mixture of anti-Markovnikov and Markovnikov hydrosilylation by their characteristic proton signals (a multiplet at 0.75 ppm for Anti-Markovnikov product; a doublet at 1.3 ppm for Markovnikov product)

Example 20

Silylation of Allyl(Poly)Ether (Y10227) with (EtO)₃SiH Using $^{Me}$APDICoNs

In a nitrogen-filled drybox, a scintillation vial was charged with 0.279 g of Y10227 (6.88% vinyl content) and approximately 0.001 g of $^{Me}$APDICoNs (0.004 mmol, 1 mol %), (EtO)₃SiH (0.075 g, 0.457 mmol) was then added and the reaction mixture was stirred at 50° C. for 1 hour. The product mixture was quenched by exposure to air. The product mixture was filtered through silica gel and eluted with hexane. The product mixture was analyzed by $^1$H NMR spectroscopy. The $^1$H NMR (benzene-d₆) spectrum contained no olefinic peaks, and characteristic alpha-Si methylene CH₂ signals were observed at 0.71 ppm indicating formation of Anti-Markovnikov hydrosilylation product.

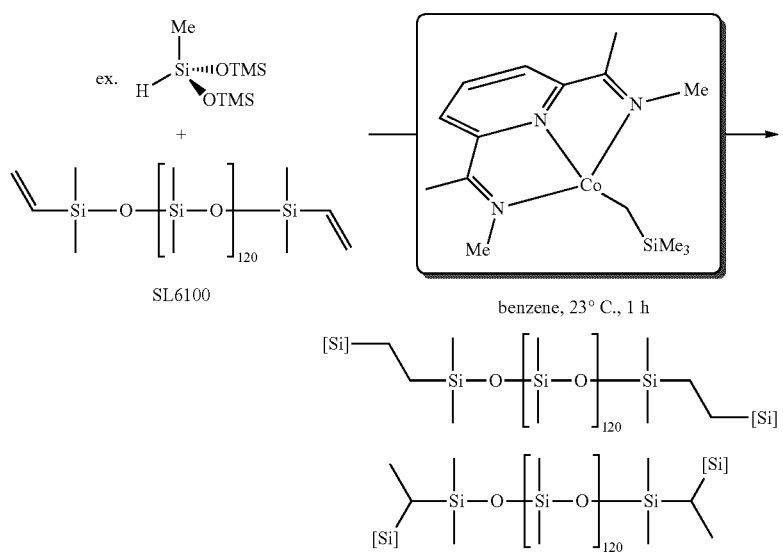

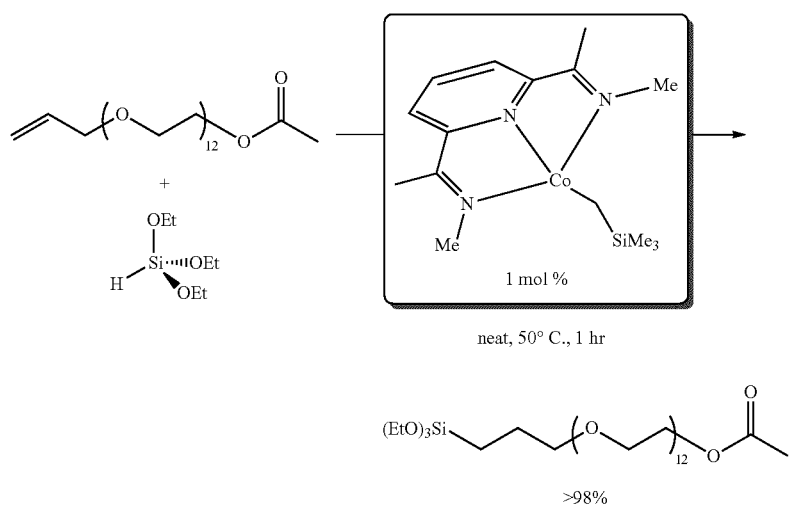

>98%

Examples 21-34

General Procedure for the Silylation of Vinylsilane with Different Silanes Using $^{Me}$APDICoNs, $^{Et}$APDICoNs or $^{Cy}$APDICoNs In a nitrogen-filled drybox, a scintillation vial was charged with 0.089 g (0.891 mmol) of trimethyl(vinyl)silane and 0.004 mmol (0.5 mol %) of cobalt catalyst (0.002 g of $^{Cy}$APDICoNs, 0.002 g of $^{Et}$APDICoNs or 0.001 g of $^{Me}$APDICoNs), 0.891 mmol of silane (0.146 g of (EtO)$_3$SiH or 0.198 g of MD$^H$M) was then added to the mixture and the reaction was stirred at room temperature for desired amount of time. The product mixture was quenched by exposure to air. The product mixture was filtered through silica gel and eluted with hexane. The resulting solution was dried under vacuum and the remaining residue was analyzed by $^1$H and $^{13}$C NMR spectroscopy.

| [Co] | [Si]—H | A | B | C |
|---|---|---|---|---|
| $^{Me}$APDICoNs | (EtO)$_3$SiH | 0 | 57 | 43 |
|  | MD$^H$M | 0 | 76 | 24 |
| $^{Et}$APDICoNs | (EtO)$_3$SiH | 0 | 33 | 67 |
|  | MD$^H$M | 1 | 60 | 39 |
| $^{Cy}$APDICoNs | (EtO)$_3$SiH | 0 | 3 | 97 |
|  | MD$^H$M | 8 | 84 | 8 |

| [Co] | t (95% conv.) | [Si] | [Si]'—H | A | B | C | D |
|---|---|---|---|---|---|---|---|
| $^{Me}$APDICoNs | 1 h | SiMe(OSiMe$_3$)$_2$ | (EtO)$_3$SiH | 38.5 | — | 61.5 | — |
|  | 1 h | SiMe(OSiMe$_3$)$_2$ | MD$^H$M | 23 | — | 77 | — |
|  | 1 h | Si(OEt)$_3$ | (EtO)$_3$SiH | 8.5 | — | 91.5 | — |
|  | 1 h | Si(OEt)$_3$ | MD$^H$M | 40 | — | 60 | — |
| $^{Cy}$APDICoNs | 1 h | SiMe(OSiMe$_3$)$_2$ | (EtO)$_3$SiH | 72 | — | 27 | 1 |
|  | 12 h | SiMe(OSiMe$_3$)$_2$ | MD$^H$M | 2.5 | 16 | 30 | 51.5 |
|  | 1 h | Si(OEt)$_3$ | (EtO)$_3$SiH | — | 43 | — | 57 |
|  | 12 h | Si(OEt)$_3$ | MD$^H$M | 14 | — | 85 | 1 |

Representative Example (21) of Hydrosilylation of Trimethyl (Vinyl)Silane with (EtO)$_3$SiH Using $^{Me}$APDICoNs According to the general procedure described above, the product is a mixture of triethoxy(2-(trimethylsilyl)ethyl)silane and triethoxy(1-(trimethylsilyl)ethyl)silane in 57:43 ratio. Characterization for triethoxy(2-(trimethylsilyl)ethyl)silane: $^1$H NMR (benzene-d$_6$, 23° C.): δ=3.81 (q, 7 Hz, 6H), 1.17 (t, 7 Hz, 9H), 0.76-0.64 (m, 4H), −0.02 (s, 9H); $^{13}$C NMR (benzene-d$_6$, 23° C.): δ=58.56, 18.64, 8.28, 3.39, −2.15 Characterization for triethoxy(1-(trimethylsilyl)ethyl)silane: $^1$H NMR (benzene-d$_6$, 23° C.): δ=3.77 (q, 7 Hz, 6H), 1.15 (t, 7 Hz, 9H), 0.20 (s, 9H), 0.06 (q, 7 Hz, 1H); $^{13}$C NMR (benzene-d$_6$, 23° C.): δ=58.57, 18.69, 8.75, 3.82, −1.10

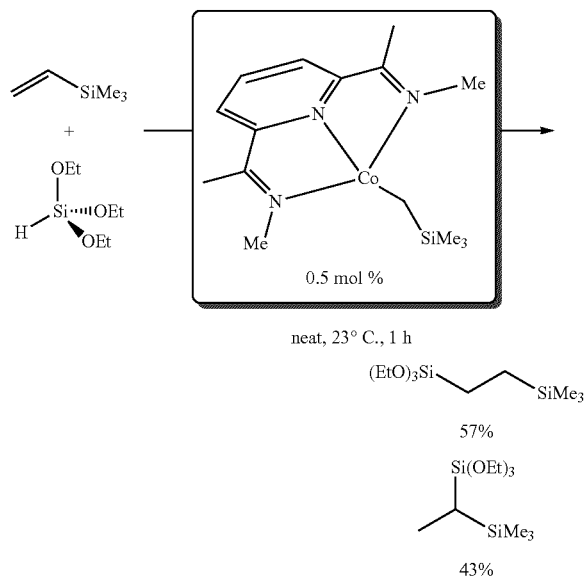

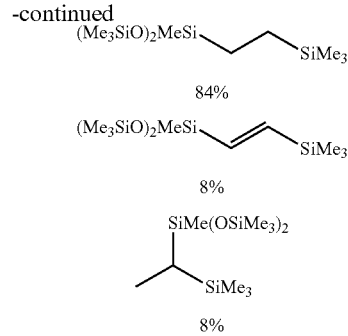

Representative Example (26) of Hydrosilylation of Trimethyl (Vinyl)Silane with MD$^H$M Using $^{Cy}$APDICoNs According to the general procedure described above, the product is a mixture of 1,1,1,3,5,5,5-heptamethyl-3-(2-(trimethylsilyl)ethyl)trisiloxane, (E)-1,1,1,3,5,5,5-heptamethyl-3-(2-(trimethylsilyl)vinyl)trisiloxane and 1,1,1,3,5,5,5-heptamethyl-3-(1-(trimethylsilyl)ethyl)trisiloxane in 84:8:8 ratio.

Characterization of 1,1,1,3,5,5,5-heptamethyl-3-(2-(trimethylsilyl)ethyl)trisiloxane: $^1$H NMR (benzene-d$_6$, 23° C.): δ=0.56-0.42 (m, 4H), 0.30-0.10 (m, br, 30H); $^{13}$C NMR (benzene-d$_6$, 23° C.): δ=10.11, 8.42, 2.14, −0.76, −2.00.

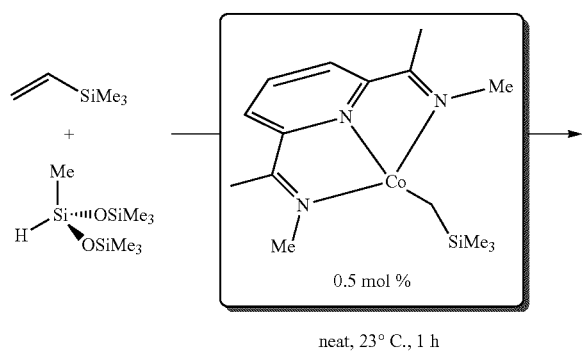

Example 35

General Procedure for Co-Catalyzed Hydrosilation of Alkynes

To a scintillation vial equipped with stir bar under nitrogen was added $^{Me}$APDICoNs (0.003 g) followed by triethoxysilane (0.149 g) and 1-octyne (100 mg, 1.00 equiv.). The vial was sealed with a cap and heated to 80° C. in an oil bath for 3 hours. After cooling to ambient temperature, the resulting dark reaction mixture was exposed to air to destroy remaining catalyst. The volatiles were removed with a stream of air and the resulting residue was diluted with a solution of 5% ethyl ether in pentane and passed through a small column of silica gel, eluting with additional 5% ether in pentane solution (5 mL). The resulting clear, colorless eluent was concentrated to give the product mixture as a clear, colorless oil (237 mg, 95%). Analysis of the product by both $^1$H and $^{13}$C NMR established the product ratio shown below. All spectra are in accordance with the literature values (Bo, G. D.; Berthon-Gelloz, G.; Tinant, B.; Markó, I. E. *Organometallics* 2006, 25, 1881.)

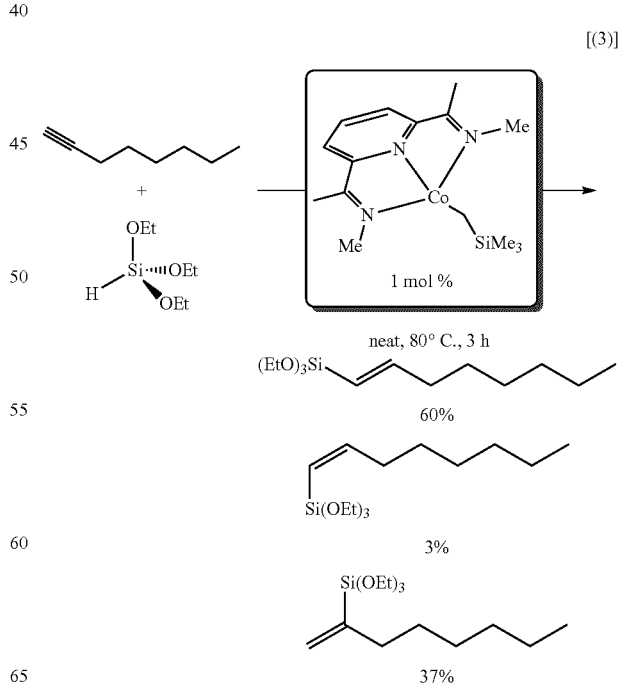

Example 36A-36C

Silylation of Propylene with Different Silanes Using ($^{Mes}$PDI)CoCH$_3$

This reaction was carried out in a manner similar to the silylation of 1-butene using 0.11 mmol of silane (0.025 g of MD$^H$M, 0.018 g of (EtO)$_3$SiH or 0.015 g of (OEt)$_2$CH$_3$SiH) 0.001 g (0.002 mmol) of ($^{Mes}$PDI)CoCH$_3$ and 5.6 mmol (50 equiv) of propylene. The non-volatiles were analyzed by NMR spectroscopy.

TABLE 12

Product Distribution for the Silylation of Propylene.

| Silane | [Si]-allyl | [Si]-propyl | Disproportionation Product |
|---|---|---|---|
| Ex 36A: MD$^H$M | 82% | 18% | None |
| Ex 36B: TES | 40% | 20% | 40% |
| Ex 36C: Me(OEt)$_2$SiH | 60% | 30% | 10% |

Characterization of Products of Example 36A 3-bis(trimethylsiloxy)methylsilyl-1-propene $^1$H NMR (CDCl$_3$): δ=0.03 (s, 3H, (OTMS)$_2$SiCH$_3$), 0.09 (s, 18H, OSi(CH$_3$)$_3$), 1.49 (d, J=8.1 Hz, 2H, SiCH$_2$CH=CH), 4.86 (d, J=6.3 Hz, 1H, CH$_2$CH=C(H)H), 4.88 (d, J=15 Hz, 1H, CH$_2$CH=C(H)H), 5.77 (m, 1H, CH$_2$CH=CH$_2$). $^{13}$C {$^1$H} NMR (CDCl$_3$): δ=−0.77 ((OTMS)$_2$SiCH$_3$), 1.97 (OSi(CH$_3$)$_3$), 25.82 (SiCH$_2$CH=CH), 113.72 (CH$_2$CH=CH$_2$), 134.28 (CH$_2$CH=CH$_2$).

1-bis(trimethylsiloxy)methylsilylpropane $^1$H NMR (CDCl$_3$): δ=0.00 (s, 3H, (OTMS)$_2$SiCH$_3$), 0.09 (s, 18H, OSi(CH$_3$)$_3$), 0.46 (m, 2H, SiCH$_2$CH$_2$CH$_3$), 0.95 (t, 3H, SiCH$_2$CH$_2$CH$_3$), 1.36 (m, 2H, SiCH$_2$CH$_2$CH$_3$). $^{13}$C {$^1$H} NMR (CDCl$_3$): δ=−0.07 ((OTMS)$_2$SiCH$_3$), 1.97 (OSi(CH$_3$)$_3$), 16.75 (SiCH$_2$CH$_2$CH$_3$), 18.05 (SiCH$_2$CH$_2$CH$_3$), 20.37 (SiCH$_2$CH$_2$CH$_3$).

Characterization of Products of Example 36B 3-triethoxysilyl-1-propene $^1$H NMR (CDCl$_3$): δ=1.22 (t, 9H, OCH$_2$CH$_3$), 1.67 (d, 2H, SiCH$_2$CH=CH), 3.84 (q, 6H, OCH$_2$CH$_3$), 4.90-5.05 (d, 2H, CH$_2$CH=CH$_2$), 5.81 (m, 1H, CH$_2$CH=CH$_2$). $^{13}$C {$^1$H} NMR (CDCl$_3$): δ=18.36 (OCH$_2$CH$_3$), 19.34 (SiCH$_2$CH=CH), 58.73 to (OCH$_2$CH$_3$), 114.85 (CH$_2$CH=CH$_2$), 132.80 (CH$_2$CH=CH$_2$).

1-triethoxysilylpropane $^1$H NMR (CDCl$_3$): δ=0.63 (m, 2H, SiCH$_2$CH$_2$CH$_3$), 0.97 (t, 3H, SiCH$_2$CH$_2$CH$_3$), 1.22 (t, 9H, OCH$_2$CH$_3$), 1.45 (m, 2H, SiCH$_2$CH$_2$CH$_3$), 3.84 (q, 6H, OCH$_2$CH$_3$). $^{13}$C {$^1$H} NMR (CDCl$_3$): δ=10.94 (SiCH$_2$CH$_2$CH$_3$), 12.92 (SiCH$_2$CH$_2$CH$_3$), 16.50 (SiCH$_2$CH$_2$CH$_3$), 18.43 (OCH$_2$CH$_3$), 58.40 (OCH$_2$CH$_3$).

Characterization of Products of Example 36C 3-diethoxymethylsilyl-1-propene $^1$H NMR (CDCl$_3$): δ=0.11 (s, 3H, SiCH$_3$), 1.19 (t, 6H, OCH$_2$CH$_3$), 1.63 (d, 2H, SiCH$_2$CH=CH), 3.76 (q, 4H, OCH$_2$CH$_3$), 4.88 (d, 1H, CH$_2$CH=C(H)H), 4.93 (d, 1H, CH$_2$CH=C(H)H), 5.80 (m, 1H, CH$_2$CH=CH$_2$). $^{13}$C {$^1$H} NMR (CDCl$_3$): δ=−5.19 (SiCH$_3$), 18.44 (OCH$_2$CH$_3$), 21.92 (SiCH$_2$CH=CH), 58.41 (OCH$_2$CH$_3$), 114.45 (CH$_2$CH=CH$_2$), 133.36 (CH$_2$CH=CH$_2$).

1-diethoxymethylsilylpropane $^1$H NMR (CDCl$_3$): δ=0.08 (s, 3H, SiCH$_3$), 0.59 (m, 2H, SiCH$_2$CH$_2$CH$_3$), 0.94 (t, 3H, SiCH$_2$CH$_2$CH$_3$), 1.19 (t, 6H, OCH$_2$CH$_3$), 1.38 (m, 2H, SiCH$_2$CH$_2$CH$_3$), 3.76 (q, 4H, OCH$_2$CH$_3$). $^{13}$C {$^1$H} NMR (CDCl$_3$): δ=−4.76 (SiCH$_3$), 16.37 (SiCH$_2$CH$_2$CH$_3$), 16.53 (SiCH$_2$CH$_2$CH$_3$), 18.07 (SiCH$_2$CH$_2$CH$_3$), 18.50 (OCH$_2$CH$_3$), 58.13 (OCH$_2$CH$_3$).

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A process for producing a silylated product comprising reacting a mixture comprising (a) an unsaturated compound containing at least one unsaturated functional group, (b) a silyl hydride containing at least one silylhydride functional group, and (c) a catalyst, optionally in the presence of a solvent, to produce a dehydrogenative silylated product, a hydrosilylated product, or a combination of a dehydrogenative silylated product and a hydrosilylated product, wherein the catalyst is a complex of the Formula (I) or an adduct thereof;

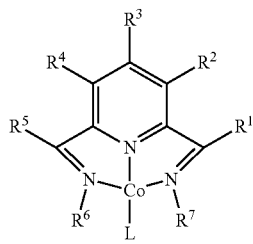

wherein each occurrence of R$^1$, R$^2$, R$^3$, R$^4$, and R$^5$ is independently hydrogen, a C1-C18 alkyl, a C1-C18 substituted alkyl, an aryl, a substituted aryl, or an inert substituent, R$^1$-R$^5$, other than hydrogen, optionally contain at least one heteroatom;
  each occurrence of R$^6$ and R$^7$ is independently a C1-C18 alkyl, a C1-C18 substituted alkyl, an aryl, or a substituted aryl, wherein R$^6$ and R$^7$ optionally contain at least one heteroatom;
  optionally any two of R$^1$, R$^2$, R$^3$, R$^4$, R$^5$, R$^6$, and R$^7$ vicinal to one another taken together may form a ring being a substituted or unsubstituted, saturated, or unsaturated cyclic structure; and
  L is CH$_2$SiR$^8$$_3$ where each occurrence of R$^8$ is independently a C1-10 alkyl or an aryl group, where R$^8$ optionally contains at least one heteroatom.

2. The process of claim 1, wherein R$^8$ is CH$_3$.
3. The process of claim 1, wherein R$^6$ and R$^7$ are independently chosen from a C1-C10 alkyl.
4. The process of claim 3, wherein R$^6$ and R$^7$ are each methyl.
5. The process of claim 3, wherein R$^6$ and R$^7$ are each ethyl.

6. The process of claim 3, wherein $R^6$ and $R^7$ are each cyclohexyl.

7. The process of claim 1, wherein $R^8$ is methyl; $R^6$ and $R^7$ are independently chosen from a C1-C10 alkyl, and $R^2$, $R^3$, and $R^4$ are each hydrogen.

8. The process of claim 1, wherein the catalyst is chosen from:

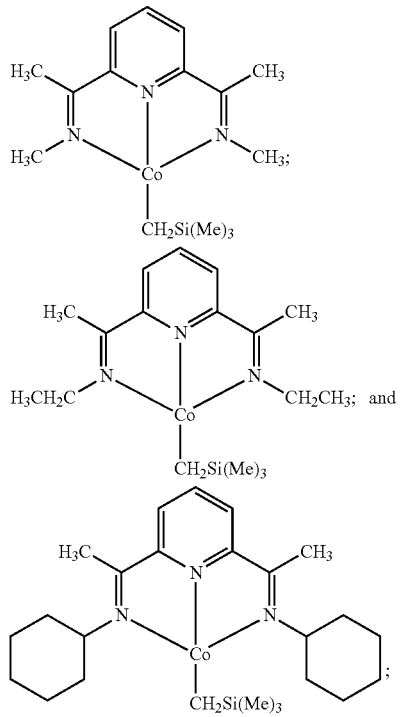

or a combination of two or more thereof.

9. The process of claim 1, wherein component (a) is chosen from an olefin, a cycloalkene, an unsaturated polyether, a vinyl-functional alkyl-capped allyl or methallyl polyether, an alkyl-capped terminally unsaturated amine, an alkyne, a terminally unsaturated acrylate or methacrylate, an unsaturated aryl ether, a vinyl-functionalized polymer or oligomer, a vinyl-functionalized silane, a vinyl-functionalized silicone, an unsaturated fatty acid, an unsaturated ester, or a combination of two or more thereof.

10. The process of claim 1, wherein component (a) is chosen from a compound of the formula:

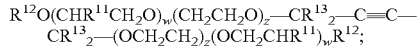

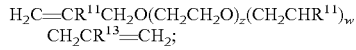

or a combination of two or more thereof, wherein $R^{10}$ is chosen from an unsaturated organic group containing from 2 to 10 carbon atoms; $R^{12}$ is chosen from hydrogen, a vinyl group, or a polyether capping group of from 1 to 8 carbon atoms; each occurrence of $R^{11}$ is independently chosen from a monovalent hydrocarbon group having 1-20 carbon atoms, an aryl group, an alkaryl, an aralkyl, a cycloalkyl group; each occurrence of $R^{13}$ is independently chosen from hydrogen, a monovalent hydrocarbon group having 1-20 carbon atoms, an aryl group, an alkaryl group, an aralkyl group, or a cycloalkyl group; each occurrence of z is 0 to 100 inclusive; and, each occurrence of w is 0 to 100 inclusive.

11. The process of claim 1, wherein component (a) is chosen from N,N-dimethylallyl amine, allyloxy-substituted polyethers, propylene, 1-butene, 1-hexene, styrene, vinylnorbornane, 5-vinyl-norbornene, 1-octadecene, cyclopentene, cyclohexene, norbornene, 3-hexene, isobutylene, 3-methyl-1-octene, polybutadiene, polyisoprene, EPDM, oleic acid, linoleic acid, methyl oleate, a vinyl siloxane of the Formula (VI),

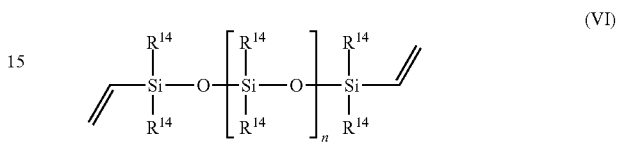

or a combination of two or more thereof, wherein each occurrence of $R^{14}$ is independently a C1-C18 alkyl, C1-C18 substituted alkyl, vinyl, aryl, or a substituted aryl, and n is greater than or equal to zero.

12. The process of claim 1, wherein component (b) is chosen from a compound of the formula $R_aSiH_{4-a}$, $(RO)_aSiH_{4-a}$, $HSiR_a(OR)_{3-a}$, $R_3Si(CH_2)_f(SiR_2O)_kSiR_2H$, $(RO)_3Si(CH_2)_f(SiR_2O)_kSiR_2H$, $Q_uT_vT_p^HD_wD^H_xM^H_yM_z$, $R_3Si(CH_2R)_xSiOSiR_2(OSiR_2)_yOSiR_2H$, or combinations of two or more thereof where each occurrence of R is independently a C1-C18 alkyl, a C1-C18 substituted alkyl, wherein R optionally contains at least one heteroatom, each occurrence of a independently has a value from 0 to 3, f has a value of 1 to 8, k has a value of 1 to 11, each of p, u, v, y and z independently has a value from 0 to 20, w and x are from 0 to 3000, provided that p+x+y equals 1 to 1000 and the valences of the all the elements in the silyl hydride are satisfied, M represents a monofunctional group of formula $R'_3SiO_{1/2}$, D represents a difunctional group of formula $R'_2SiO_{2/2}$, T represents a trifunctional group of formula $R'SiO_{3/2}$, Q represents a tetrafunctional group of formula $SiO_{4/2}$, an $M^H$ represents $HR'_2SiO_{1/2}$, $T^H$ represents $HSiO_{3/2}$, and $D^H$ represents $R'HSiO_{2/2}$; each occurrence of R' is independently C1-C18 alkyl, C1-C18 substituted alkyl, wherein R' optionally contains at least one heteroatom; x is 1-8, and y is 0-10.

13. The process of claim 1, wherein the catalyst is present in an amount of from 0.01 mole percent to 10 mole percent based on the molar quantity of the unsaturated compound to be reacted.

14. The process of claim 1, wherein the process is conducted at a temperature of between about 0° C. and about 300° C.

15. The process of claim 1, wherein the complex is immobilized on a support.

16. The complex of claim 15, wherein the support is chosen from carbon, silica, alumina, $MgCl_2$, zirconia, polyethylene, polypropylene, polystyrene, poly(aminostyrene), sulfonated polystyrene, or a combination of two or more thereof.

17. A process for producing a hydrosilylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the dehydrogenative silylated product, and/or hydrosilylated product wherein the catalyst is a complex of the Formula (I) or an adduct thereof;

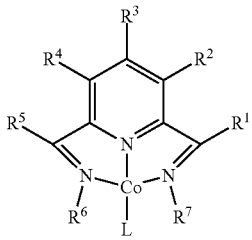

(I)

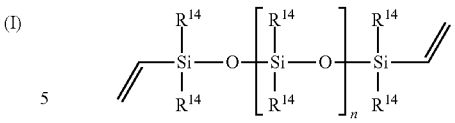

wherein each occurrence of $R^1$, $R^2$, $R^3$, $R^4$, and $R^5$ is independently hydrogen, a C1-C18 alkyl, a C1-C18 substituted alkyl, an aryl, a substituted aryl, or an inert substituent, wherein $R^1$-$R^5$, other than hydrogen, optionally contain at least one heteroatom;

each occurrence of $R^6$ and $R^7$ is independently a C1-C18 alkyl, a C1-C18 substituted alkyl, an aryl, a substituted aryl, wherein $R^6$ and $R^7$ optionally contain at least one heteroatom;

optionally any two of $R^1$, $R^2$, $R^3$, $R^4$, $R^5$, $R^6$, and $R^7$ vicinal to one another taken together may form a ring being a substituted or unsubstituted, saturated, or unsaturated cyclic structure; and L is $CH_2SiR^8_3$ where each $R^8$ is independently a C1-10 alkyl or aryl group optionally containing at least one heteroatom.

18. The process of claim 17, wherein component (a) is chosen from an olefin, a cycloalkene, an alkyl-capped allyl polyether, a vinyl-functional alkyl-capped allyl or methallyl polyether, an alkyl-capped terminally unsaturated amine, an alkyne, a terminally unsaturated acrylate or methacrylate, an unsaturated aryl ether, a vinyl-functionalized polymer or oligomer, a vinyl-functionalized silane, a vinyl-functionalized silicone, an unsaturated fatty acid, an unsaturated ester, or a combination of two or more thereof; and component (b) is chosen from a compound of the formula $R_aSiH_{4-a}$, $(RO)_aSiH_{4-a}$, $HSiR_a(OR)_{3-a}$, $R_3Si(CH_2)_f(SiR_2O)_kSiR_2H$, $(RO)_3Si(CH_2)_f(SiR_2O)_kSiR_2H$, $Q_uT_vT_p^HD_wD^H_xM^H_yM_z$, $R_3Si(CH_2R)_xSiOSiR_2(OSiR_2)_yOSiR_2H$ and combinations of two or more thereof where each occurrence of R is independently a C1-C18 alkyl, a C1-C18 substituted alkyl, wherein R optionally contains at least one heteroatom, each occurrence of a independently has a value from 1 to 3, f has a value of 1 to 8, k has a value of 1 to 11, each of p, u, v, y and z independently has a value from 0 to 20, w and x are from 0 to 500, provided that p+x+y equals 1 to 500 and the valences of the all the elements in the silyl hydride are satisfied, M represents a monofunctional group of formula $R'_3SiO_{1/2}$, a D represents a difunctional group of formula $R'_2SiO_{2/2}$, T represents a trifunctional group of formula $R'SiO_{3/2}$, Q represents a tetrafunctional group of formula $SiO_{4/2}$, an $M^H$ represents $HR'_2SiO_{1/2}$, $T^H$ represents $HSiO_{3/2}$, and $D^H$ represents $R'HSiO_{2/2}$; each occurrence of R' is independently a C1-C18 alkyl, a C1-C18 substituted alkyl, wherein R' optionally contains at least one heteroatom.

19. The process of claim 17, wherein component (a) is chosen from a vinyl-functionalized silane, a vinyl-functionalized silicone, or a combination thereof.

20. The process of claim 17, wherein component (a) is chosen from a vinyl siloxane of the formula

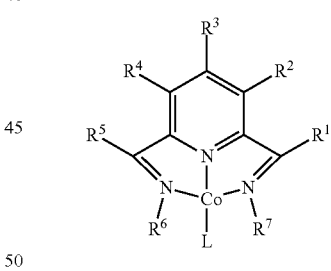

wherein each occurrence of $R^{14}$ is independently a C1-C18 alkyl, a C1-C18 substituted alkyl, a vinyl, an aryl, a substituted aryl, and n is greater than or equal to zero.

21. The process of claim 17, wherein $R^6$ and $R^7$ are each methyl.

22. The process of claim 17, wherein component (b) comprises a trialkoxy silyl hydride.

23. The process of claim 22, wherein component (a) is chosen from an olefin, a cycloalkene, an alkyl-capped allyl polyether, a vinyl-functional alkyl-capped allyl or methallyl polyether, an alkyl-capped terminally unsaturated amine, an alkyne, a terminally unsaturated acrylate or methacrylate, an unsaturated aryl ether, a vinyl-functionalized polymer or oligomer, a vinyl-functionalized silane, a vinyl-functionalized silicone, an unsaturated fatty acid, an unsaturated ester, or a combination of two or more thereof.

24. The process of claim 17, wherein the catalyst is present in an amount of from 0.01 mole percent to 10 mole percent based on the molar quantity of the unsaturated compound to be reacted.

25. The process of claim 17, wherein the process is conducted at a temperature of between about 0° C. and about 300° C.

26. A process for producing a crosslinked material, comprising reacting a mixture comprising (a) a silyl-hydride containing polymer, (b) a mono-unsaturated olefin or an unsaturated polyolefin, or combinations thereof and (c) a catalyst, optionally in the presence of a solvent, in order to produce the crosslinked material, wherein the catalyst is a complex of the Formula (I) or an adduct thereof:

wherein each occurrence of $R^1$, $R^2$, $R^3$, $R^4$, and $R^5$ is independently hydrogen, a C1-C18 alkyl, a C1-C18 substituted alkyl, an aryl, a substituted aryl, or an inert substituent, wherein $R^1$-$R^5$, other than hydrogen, optionally contain at least one heteroatom;

each occurrence of $R^6$ and $R^7$ is independently a C1-C18 alkyl, a C1-C18 substituted alkyl, aryl or substituted aryl, wherein $R^6$ and $R^7$ optionally contain at least one heteroatom;

optionally any two of $R^1$, $R^2$, $R^3$, $R^4$, $R^5$, $R^6$, and $R^7$ vicinal to one another taken together may form a ring being a substituted or unsubstituted, saturated, or unsaturated cyclic structure; and L is $CH_2SiR^8_3$ where each $R^8$ is independently a C1-10 alkyl or aryl group optionally containing at least one heteroatom.

27. The process of claim 26, wherein the reaction is conducted under an inert atmosphere.

28. The process of claim 26, wherein the reaction is conducted in the presence of a solvent selected from the group consisting of hydrocarbons, halogenated hydrocarbons, ethers, and combinations thereof.

29. The process of claim 26, wherein the reaction is carried out at a temperature of 0° C. to 300° C.

30. The process of claim 26, wherein the catalyst is present in an amount of from about 0.1 mol % to about 5 mol %.

* * * * *